United States Patent
Owen

(10) Patent No.: US 10,159,464 B2
(45) Date of Patent: *Dec. 25, 2018

(54) SEPARABLE BEAMFORMING FOR ULTRASOUND ARRAY

(71) Applicant: University of Virginia Patent Foundation, Charlottesville, VA (US)

(72) Inventor: Kevin Owen, Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 242 days.

This patent is subject to a terminal disclaimer.

(21) Appl. No.: 15/256,068

(22) Filed: Sep. 2, 2016

(65) Prior Publication Data

US 2017/0100097 A1 Apr. 13, 2017

Related U.S. Application Data

(63) Continuation of application No. 14/124,153, filed as application No. PCT/US2012/041392 on Jun. 7, 2012, now Pat. No. 9,433,398.
(Continued)

(51) Int. Cl.
*A61B 8/00* (2006.01)
*G01S 7/52* (2006.01)
(Continued)

(52) U.S. Cl.
CPC ............ *A61B 8/4494* (2013.01); *A61B 8/145* (2013.01); *A61B 8/4427* (2013.01); *A61B 8/461* (2013.01);
(Continued)

(58) Field of Classification Search
CPC ..... A61B 8/4494; A61B 8/145; A61B 8/4427; A61B 8/461; A61B 8/5207; A61B 8/56;
(Continued)

(56) References Cited

U.S. PATENT DOCUMENTS

| 5,433,202 A | 7/1995 | Mitchell et al. |
| 5,549,111 A | 8/1996 | Wright et al. |

(Continued)

FOREIGN PATENT DOCUMENTS

| DE | 112012002629 T5 | 4/2014 |
| JP | 2014515980 A | 7/2014 |

(Continued)

OTHER PUBLICATIONS

"U.S. Appl. No. 14/124,153, Non Final Office Action dated Sep. 14, 2015", 23 pgs.

(Continued)

*Primary Examiner* — Rochelle Turchen
*Assistant Examiner* — Joanne Hoffman
(74) *Attorney, Agent, or Firm* — Schwegman Lundberg & Woessner, P.A.

(57) ABSTRACT

Ultrasonic imaging apparatus or techniques can include obtaining at least an approximation of samples of reflected ultrasonic energy and constructing a representation of an imaging plane within the tissue region. Such apparatus or techniques can include separately determining, for respective focusing locations respective first sums of at least approximated complex samples of reflected ultrasonic energy obtained via respective first lines of transducers, and separately determining, for the specified focusing location, a second sum of at least some the respective first sums of at least approximated complex samples of reflected ultrasonic energy, the second sum corresponding to a second line of transducers in the ultrasonic transducer array. The separately determining the first or second sums of at least approximated complex samples can include phase-rotating at least some of the complex samples. The second line of transducers can be orthogonal to respective first lines in the transducer plane.

18 Claims, 14 Drawing Sheets

Related U.S. Application Data

(60) Provisional application No. 61/559,647, filed on Nov. 14, 2011, provisional application No. 61/494,537, filed on Jun. 8, 2011.

(51) Int. Cl.
  *G01S 15/89* (2006.01)
  *G10K 11/34* (2006.01)
  *A61B 8/08* (2006.01)
  *A61B 8/14* (2006.01)

(52) U.S. Cl.
  CPC ............ *A61B 8/483* (2013.01); *A61B 8/5207* (2013.01); *A61B 8/56* (2013.01); *G01S 7/52047* (2013.01); *G01S 15/8927* (2013.01); *G10K 11/346* (2013.01); *A61B 8/08* (2013.01); *A61B 8/14* (2013.01); *A61B 8/4488* (2013.01)

(58) Field of Classification Search
  CPC ... A61B 8/52047; A61B 8/8927; A61B 8/346; A61B 8/486
  See application file for complete search history.

(56) References Cited

U.S. PATENT DOCUMENTS

| | | |
|---|---|---|
| 6,183,419 B1 | 2/2001 | Wildes |
| 8,093,782 B1 | 1/2012 | Hossack |
| 9,433,398 B2 | 9/2016 | Owen |
| 2003/0013955 A1 | 1/2003 | Poland |
| 2003/0028113 A1 | 2/2003 | Gilbert et al. |
| 2006/0052697 A1 | 3/2006 | Hossack et al. |
| 2006/0100516 A1 | 5/2006 | Hossack et al. |
| 2006/0241434 A1 | 10/2006 | Shimazaki |
| 2007/0016044 A1 | 1/2007 | Blalock et al. |
| 2009/0048519 A1 | 2/2009 | Hossack et al. |
| 2009/0264757 A1 | 10/2009 | Yang et al. |
| 2009/0299184 A1 | 12/2009 | Walker et al. |
| 2010/0063399 A1 | 3/2010 | Walker et al. |
| 2010/0268086 A1 | 10/2010 | Walker et al. |
| 2011/0137175 A1 | 6/2011 | Hossack et al. |
| 2012/0029356 A1 | 2/2012 | Hossack et al. |
| 2012/0053460 A1 | 3/2012 | Blalock et al. |
| 2014/0200456 A1 | 7/2014 | Owen |

FOREIGN PATENT DOCUMENTS

| | | |
|---|---|---|
| WO | WO-03075769 A1 | 9/2003 |
| WO | WO-2004064619 A2 | 8/2004 |
| WO | WO-2004064620 A2 | 8/2004 |
| WO | WO-2004065978 A2 | 8/2004 |
| WO | WO-2006042067 A2 | 4/2006 |
| WO | WO-2010021709 A1 | 2/2010 |
| WO | WO-2012170714 A1 | 12/2012 |

OTHER PUBLICATIONS

"U.S. Appl. No. 14/124,153, Notice of Allowance dated Apr. 26, 2016", 5 pgs.
"U.S. Appl. No. 14/124,153, Preliminary Amendment filed Dec. 5, 2013", 3 pgs.
"U.S. Appl. No. 14/124,153, PTO Response to Rule 312 Communication dated Jul. 13, 2016", 2 pgs.
"U.S. Appl. No. 14/124,153, Response filed Mar. 11, 2016 to Non Final Office Action dated Sep. 14, 2015", 18 pgs.
"International Application Serial No. PCT/US2012/041392, International Preliminary Report on Patentability dated Dec. 27, 2013", 8 pgs.
"International Application Serial No. PCT/US2012/041392, Search Report dated Sep. 24, 2012", 3 pgs.
"International Application Serial No. PCT/US2012/041392, Written Opinion dated Sep. 24, 2012", 7 pgs.
Dhanantwari, A. C, et al., "An efficient 3D beamformer implementation for real-time 4D ultrasound systems deploying planar array probes", 2004 IEEE Ultrasonics Symposium, vol. 2, (2004), 1421-1424.
Hall, Timothy J, et al., "A Taylor Series Expansion of Time Savings in Accurate Computation of Focused Ultrasound Pressure Fields", Ultrasonic Imaging 9, (1987), 203-219.
Murino, V., et al., "Underwater 3D imaging by FFT dynamic focusing beamforming", IEEE International Conference Image Processing, 1994. Proceedings. ICIP-94., vol. 1, (19994), 890-894.
Owen, Kevin, et al., "Application of X-Y Separable 2-D Array Beamforming for Increased Frame Rate and Energy Efficiency in Handheld Devices", (Jul. 2012), 1332-1343.
Palmese, M., et al., "Digital Near Field Beamforming for Efficient 3-D Underwater Acoustic Image Generation", IEEE International Workshop on Imaging Systems and Techniques, 2007. IST '07., (2007), 1-5.
Szabo, T. L, "Chapter 6—Beamforming", Diagnostic Ultrasound Imaging: Inside Out, Burlington, MA: Elsevier Academic Press, (2004), 140-148.
Tawfik, A., "A generic processing structure decomposing the beamforming process of 2-D and 3-D arrays of sensors into sub-sets of coherent process", Proceedings of the Sixteenth National Radio Science Conference, 1999. NRSC '99., (1999), 1-8.
Wall, K., et al., "P2B-7 Development of a Versatile Signal Processing Board for Real-Time 3D Beamforming", IEEE Ultrasonics Symposium, 2007, (2007), 1526-1528.
Yang, Ming, et al., "Separable Beamforming for 3-D Synthetic Aperture Ultrasound Imaging", (2013), 1-6.
Zhang, F., et al., "Parallelization and performance of 3D ultrasound imaging beamforming algorithms on modern clusters", Proceedings of the 16th international conference on Supercomputing, (2002), 294-304.

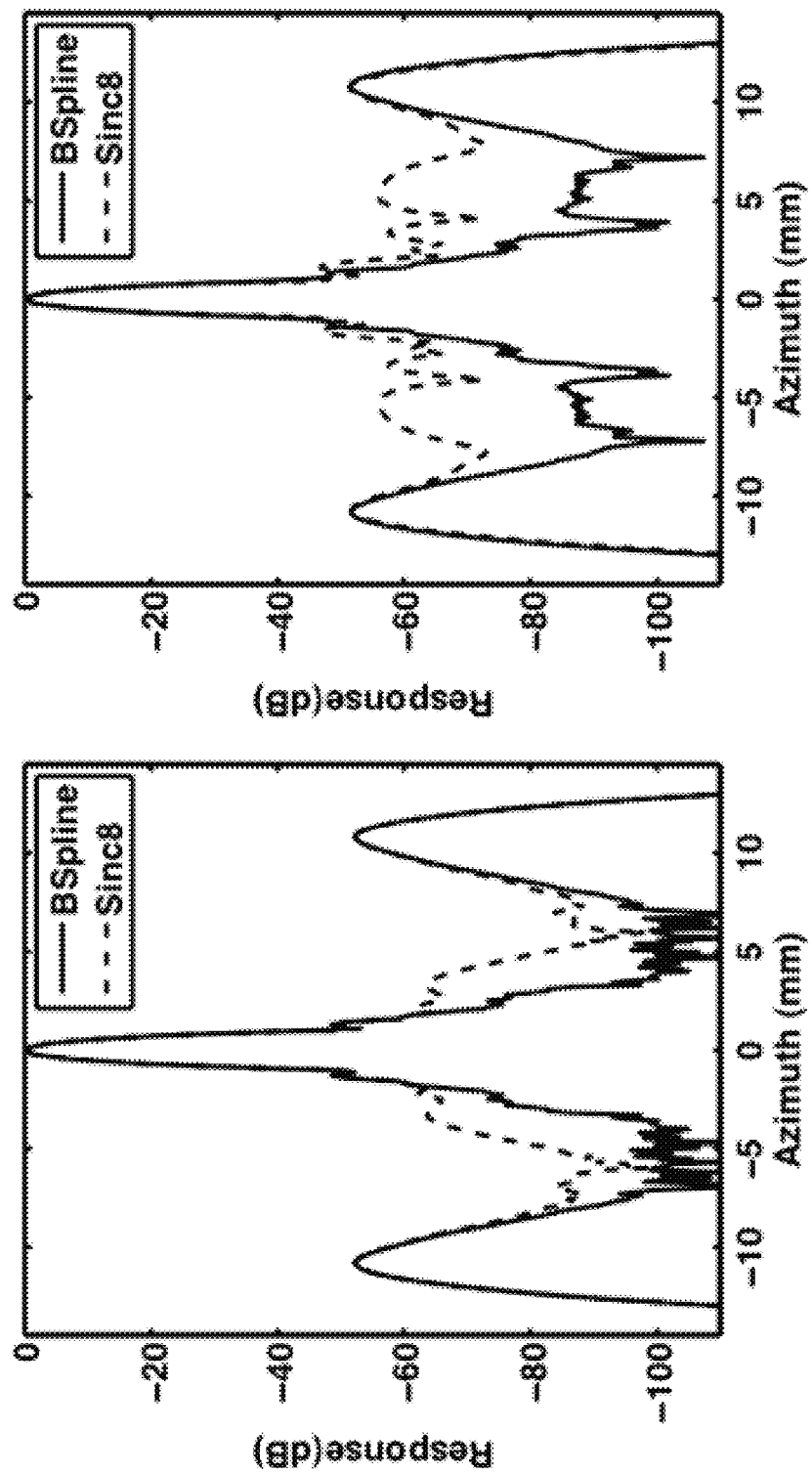

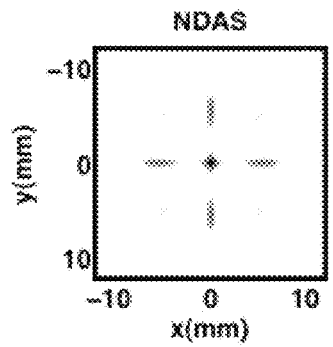 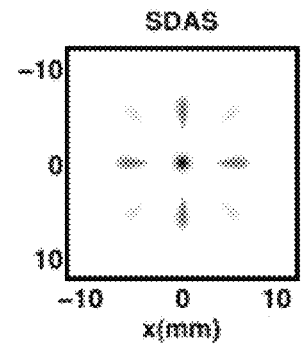 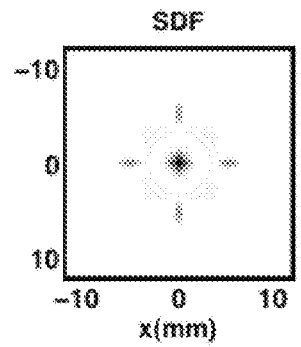
FIG. 8A       FIG. 8B       FIG. 8C
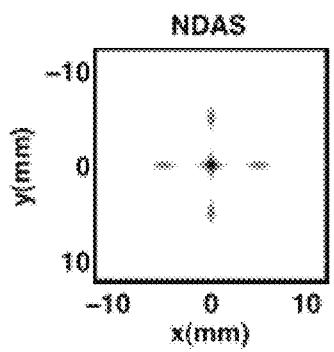 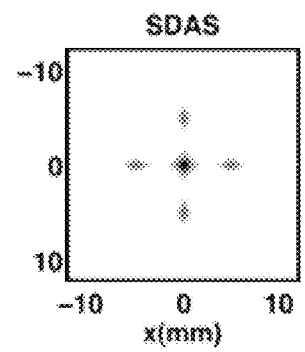 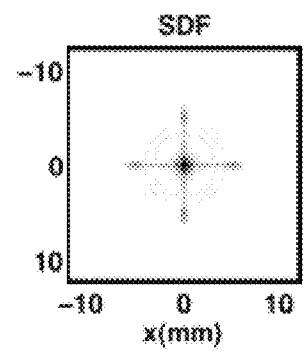
FIG. 8D       FIG. 8E       FIG. 8F
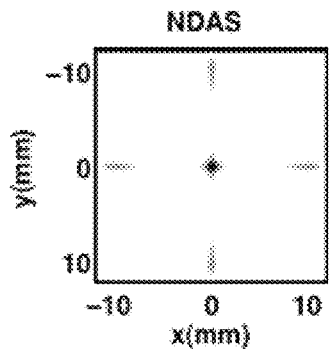 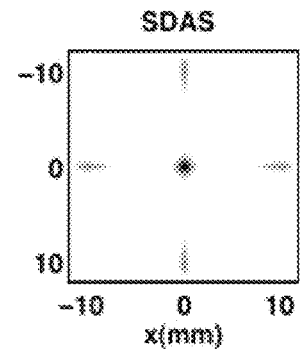 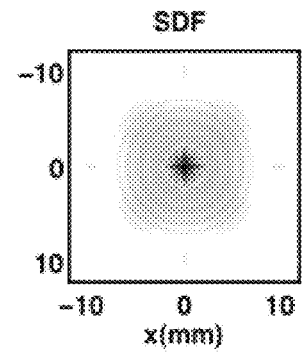
FIG. 8G       FIG. 8H       FIG. 8I

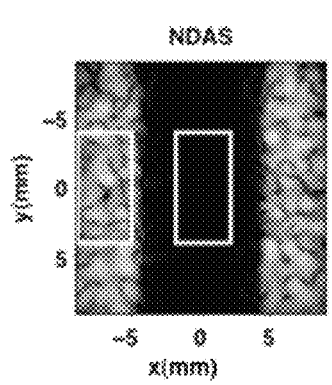 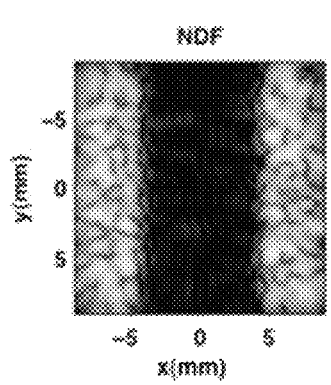 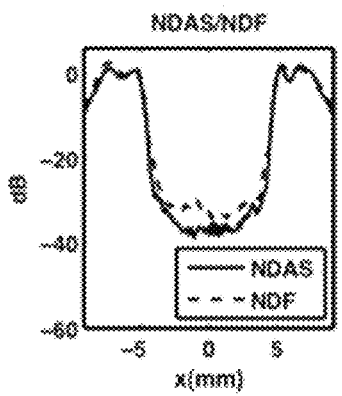
*FIG. 9A*   *FIG. 9B*   *FIG. 9C*
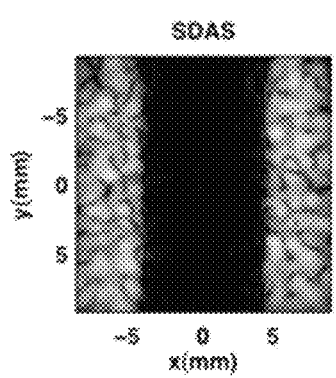 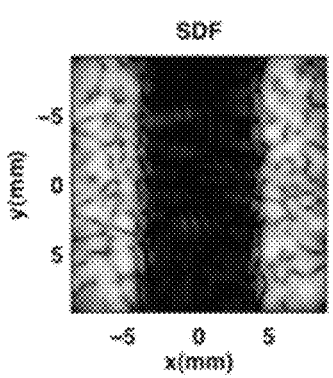 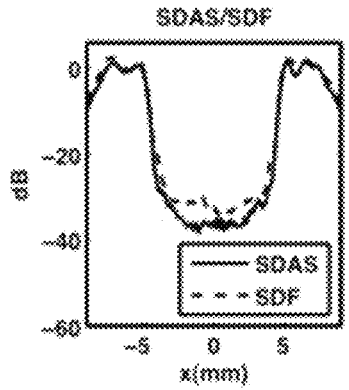
*FIG. 9D*   *FIG. 9E*   *FIG. 9F*

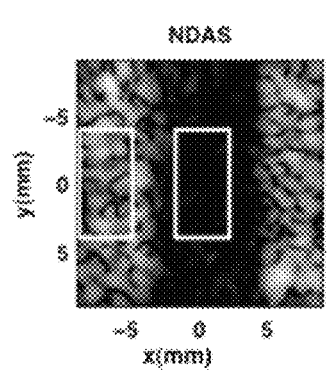 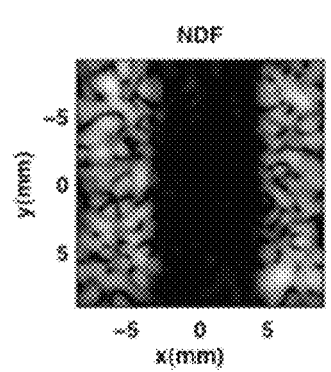 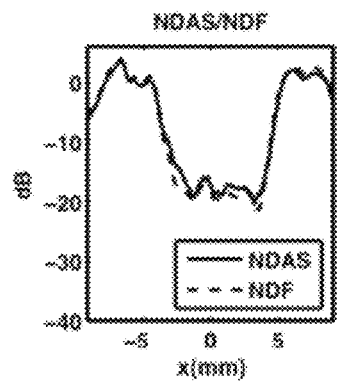
*FIG. 11A*   *FIG. 11B*   *FIG. 11C*
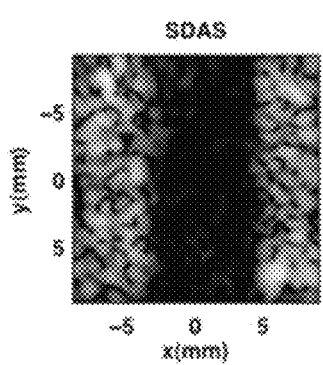 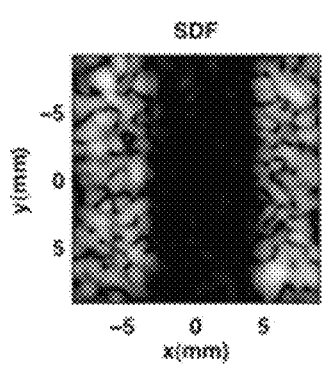 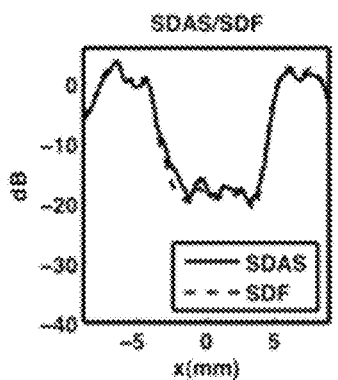
*FIG. 11D*   *FIG. 11E*   *FIG. 11F*

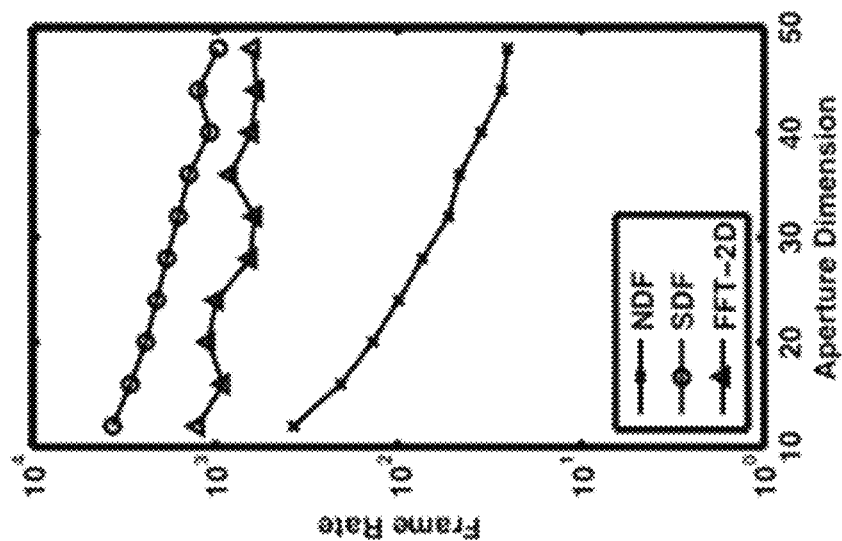
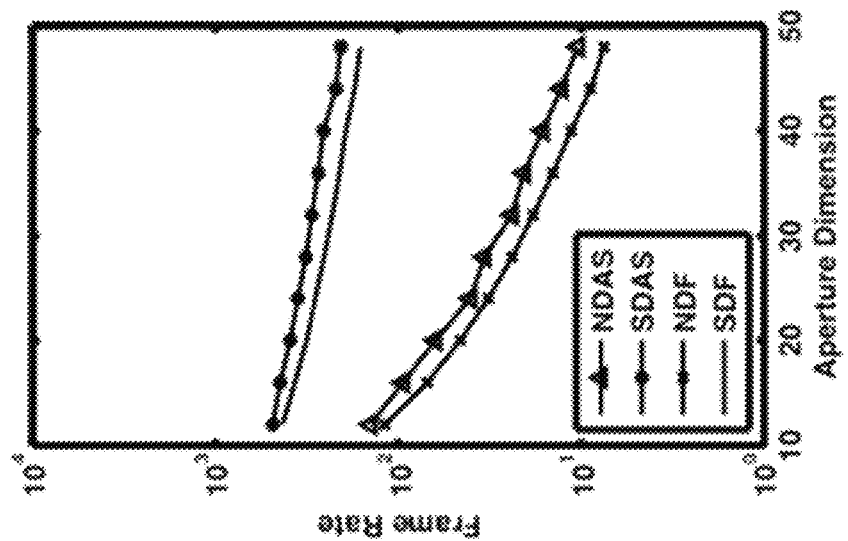
FIG. 12A
FIG. 12B

SEPARABLE BEAMFORMING FOR ULTRASOUND ARRAY

CLAIM OF PRIORITY

This application is a continuation of U.S. patent application Ser. No. 14/124,153, filed on Mar. 14, 2014, which application is a U.S. National Stage Filing under 35 U.S.C. § 371 from International Patent Application Serial No. PCT/US2012/041392 filed on Jun. 7, 2012, and published on Dec. 13, 2012 as WO 2012/170714, which claims the benefit of priority of U.S. Provisional Patent Application Ser. No. 61/494,537, titled "Method, System and Computer Program Product for Separable Approximate 2D Array Beamforming for Improved Frame Rate and Energy Efficiency," filed on Jun. 8, 2011, and benefit of priority is also hereby claimed to U.S. Provisional Patent Application Ser. No. 61/559,647, titled "Method, System and Computer Program Product for Separable Approximate 2D Array Beamforming for Improved Frame Rate and Energy Efficiency," filed on Nov. 14, 2011, each of which is hereby incorporated by reference herein in its respective entirety, and the benefit of each of which is hereby presently claimed.

BACKGROUND

Medical diagnostic ultrasound occupies an important role in cardiac, fetal, and breast imaging, among other applications. For example, ultrasound's real-time nature and lack of ionizing radiation can make it more attractive than other alternatives. Unfortunately, high levels of image clutter can present a significant problem for certain patients, and diffraction effects can limit spatial resolution (e.g., to no better than hundreds of microns). For example, dynamic focusing can be used to approach the predicted theoretical diffraction limit. Using generally-available approaches, such focusing can unacceptably increase cost or complexity of the imaging system.

Generally, the resolution limit for ultrasound is assumed to be no better than $\lambda z/D$, where can represent the ultrasound acoustic wavelength, z can represent the range to a target to be imaged, and D can represent an aperture size corresponding to the ultrasonic transducer. Thus, at least two routes can be used to improve resolution. The first can be to increase the operating frequency and thereby reduce the wavelength, $\lambda$. Such wavelength reduction works well at shallow depths, but can be limited by frequency dependent attenuation as the depth of the region of interest is increased. As the operating frequency increases, the signal to noise ratio (SNR) can also decrease, until it falls too low to form useful images. In one approach, coded excitation can mitigate this effect, but a tradeoff between resolution and SNR still exists. In another approach, resolution can be increased by expanding the imaging aperture, at least up to the point where an f-number (e.g., z/D) approaches 0.5. While aperture growth can be broadly effective, a practical limit can exist since the aperture cannot be made unreasonably large.

The past decade has seen two-dimensional (2D) arrays progress from research curiosities to common clinical tools. The majority of 2D array applications have been in cardiology for rapid volume acquisition. Such 21) array systems can include many active elements, and can include integrated circuitry within the probe assembly.

OVERVIEW

Generally, ultrasound imaging apparatus that can include two dimensional arrays of transducer elements can have costs that exceed tens of thousands of dollars. Such 2D arrays can use sub-array beamforming techniques, but such methods generally limit resolution and contrast to below theoretical limits. A 2D-array-based scanner, such as a portable battery-powered scanner, can be made more commercially viable, such as via reducing one or more of channel count, array size, or computational demand.

In particular, 2D ultrasound transducer arrays can present significant beamforming computational challenges, such as due to the relatively high channel count and data rate associated with such beamforming. Such challenges can be even more stringent when such a 2D transducer array is included as a portion of a battery-powered hand-held device, because of power efficiency demands. The present inventor has recognized, among other things, that a 2D array beamforming technique can be decomposed into two separable line-array beamforming operations. Such a "separable" technique can be used with frequency-domain phase-based beamforming (e.g., focusing), such as to perform scanning or image reconstruction of a specified region of tissue, such as a volume of tissue. Such a "separable" technique can reduce computational demand as compared to other approaches.

In an example, an ultrasound imaging system can construct a representation of a portion of a tissue region (e.g., an imaging plane, such as a C-mode imaging plane, or an arbitrary plane determined using information obtained from multiple C-mode representations), such as using a near-field separable beamforming technique. Such a technique can include one or more of a delay-and-sum (DAS) beamforming approach, or, to save on computation demand, such as at the cost of quality, a phase-rotation-based beamforming method. Such a phase-rotation-based technique can include approximating complex echo data using Direct-Sampled In-Phase Quadrature (DSIQ) sampling. Under specified conditions, in comparison to non-separable 2D imaging, up to a twenty-fold increase in frame rate is possible using a separable technique.

In an example, when a specified time-delay interpolation is used, separable DAS focusing introduces no noticeable imaging degradation under practical conditions. Focusing using a DSIQ technique can provide similar results with some degradation, but a slight modification to such DSIQ focusing can greatly increase imaging contrast, making it comparable to DAS.

In an example, ultrasonic imaging apparatus or techniques can include obtaining at least an approximation of samples of reflected ultrasonic energy and constructing a representation of an imaging plane within the tissue region. Such apparatus or techniques can include separately determining, for respective focusing locations respective first sums of at least approximated complex samples of reflected ultrasonic energy obtained via respective first lines of transducers, and separately determining, for the specified focusing location, a second sum of at least some the respective first sums of at least approximated complex samples of reflected ultrasonic energy, the second sum corresponding to a second line of transducers in the ultrasonic transducer array. The separately determining the first or second sums of at least approximated complex samples can include phase-rotating at least some of the complex samples. The second line of transducers can be orthogonal to respective first lines in the transducer plane.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 5A and 5B illustrate generally illustrative examples showing an interpolation error in respective simulated beamplots for an NDAS technique in FIG. 5A and an SDAS technique in FIG. 5B.

FIGS. 8A through 8I illustrate generally illustrative examples such as can include simulated 2D PSFs for NDAS, SDAS and SDF focusing techniques, under more difficult imaging conditions including low f-number, shallow focal depth, and increased excitation pulse frequency.

FIGS. 9A through 9F illustrate generally an illustrative example of a comparison between simulated C-mode images corresponding to NDAS, SDAS, NDF, and SDF beamforming techniques that can be obtained, such as using FIELD II including an simulated anechoic cyst phantom.

FIGS. 11A through 11F illustrate generally an illustrative example of a comparison between experimentally-obtained C-mode image slices corresponding to NDAS, SDAS, NDF, and SDF beamforming techniques.

FIGS. 12A and 12B illustrate generally an illustrative example of a comparison of attainable frame-rates versus an aperture dimension, such as can be obtained for various beamforming techniques.

DETAILED DESCRIPTION

Figure 1:
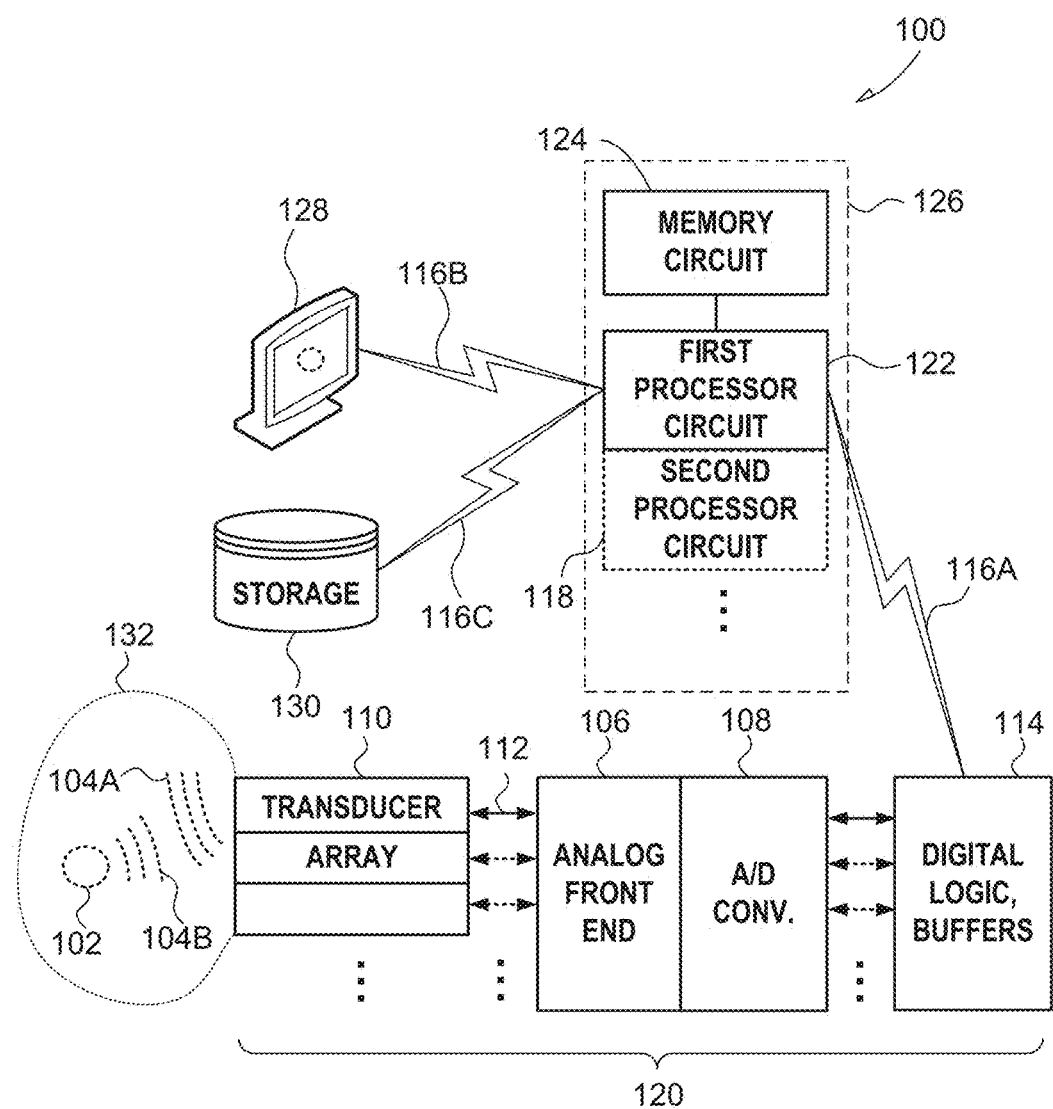
FIG. 1 illustrates generally an example of at least a portion of an ultrasonic imaging system.

Generally-available beamforming techniques can include summing weighted time-delayed echo information obtained from all channels in an aperture such as to form a single "beam" during receiving. For two-dimensional (2D) arrays that can provide echo information from a volume (e.g., including azimuth, elevation, and time/depth), such beamforming can be considered to be a spatial filtering or convolution operation. However, the computational or energy cost of such beamforming can be prohibitive when applied to 2D transducer arrays with many thousands of channels. For example, in hand-held, battery-operated systems, such energy cost can be important if such systems are specified for multi-hour battery life before recharging.

Various techniques can be used to increase a frame-refresh rate (e.g., "frame rate") of ultrasound imaging systems that include 2D transducer arrays. Such an increase in frame rate can be associated with a corresponding reduction in computational cost per frame. For example, one or more of sparse 2D arrays, synthetic aperture approaches, transmit-receive coarrays, subaperture methods, parallel beamforming or plane-wave transmit with limited-diffraction receive beam focusing can be used. In another approach, phased 2D subarray focusing, or "micro-beamforming" can be used for diagnostic ultrasound imaging with 2D arrays such as to perform partial focusing close to, or in, the transducer assembly, such as to reduce interconnect complexity or computational cost.

The present inventor has recognized, among other things, that a 2D beamforming technique can be decomposed into separate 1D line array beamforming techniques. Computational efficiencies can be achieved with such a "separable" technique by re-using the results of respective 1D beamformed partial sums multiple times. Various frequency-domain beamforming techniques can be used with a such a separable technique, such as can include using a 1D FFT in the time dimension to implement delays for narrowband signals, or using a 2D EFT in the X-Y plane, such as in some SONAR volume imaging approaches. The separable approach can also be used in near-field wide-band SONAR applications, such as using the chirp zeta transform (CZT) or the Fresnel approximation. In three-dimensional (3D) ultrasound imaging, separable techniques can include using a variation of the time-series 1D FFT acceleration method, such as implemented on a multi-node cluster of personal computers (PCs). Such real-time 3D ultrasound beamforming implementations using clusters of PCs or several Field-Programmable Gate Arrays (FPGAs) primarily target system performance, but such techniques are generally not capable of practical real-time imaging on a battery powered, hand-held system configured to obtain echo information from a fully-sampled 2D array.

In contrast, the present inventor has also recognized that separable beamformers for volume and planar (e.g., C-mode) imaging can be implemented using a hand-held system, such as can include using successive 1D convolutions in the azimuth and elevation directions (e.g., in a plane defined by a two-dimensional transducer array). In one approach, a separable delay-and-sum beamforming technique can be used, such as can include different time-delay interpolation techniques. In another approach, a 2D focusing technique can be implemented, such as for power-efficient C-mode imaging in hand-held devices including, such as using a Directly-Sampled In-phase Quadrature (DSIQ) sampling technique. Such a DSIQ technique can greatly reduce power consumption by not requiring full time-series sampling on each channel. In an illustrative example, such a DSIQ sampling technique can consume only about tens of milliwatts (mW) of power, such as for an entire 3600-channel analog front-end, as compared to about tens of milliwatts per channel for each channel in generally-available front-end systems. A DSIQ sampling technique can generally provide only limited time-delay resolution, such as due at least in part to the use of phase-rotations as approximations for time delays.

The present inventor has recognized, among other things, that for an 2D focal aperture having dimensions that can be represented by "M×N," separable focusing can yield an "MN/(M+N)" speed increase over non-separable focusing, such as producing a twenty-fold increase for a 40×40 element aperture, independent of array size. This level of performance gain is believed significant for a hand-held 2D-array ultrasound system, where intrinsic frame rate capability above about 30 frames per second can be recovered as additional battery life through a corresponding reduction in power consumption per frame.

FIG. 1 illustrates generally an example of portions of a system 100 that can include an ultrasonic imaging system, and portions of an environment in which the system 100 can be used. In an example, the system 100 can include a first processor circuit 122, a memory circuit 124, a display 128, a storage unit 130, one or more transducers 110, an analog front-end 106 coupled to an array of transducers 110, such as via a bus 112, one or more analog-to-digital (A/D) converters 108, and a digital logic circuit 114 such as including one or more buffers. In FIG. 1, one or more of the memory circuit 124, the first processor circuit 122, or one or more additional processor circuits such as a second processor circuit 118 can be included in a computer system 126. Such as computer system 126 can include a hand-held or tablet computer, a desktop computer, a laptop computer, a computer server, or a combination of one or more general purpose or special purpose computers, such as configured to obtain ultrasonic echo information from a transducer block 120, such as via a wired or wireless communication link 116A.

In an example, a region of interest 132 can include one or more actual targets such as a first target 102. The region of interest 132 can be excited (e.g., insonified, etc.) such as using energy provided by the transducer array 110, such as under the control of the first processor circuit 122. For example, a transmitted ultrasonic energy 104A can propagate through the region of interest 132, and a portion of the transmitted energy 104A can be scattered or reflected by one or more targets, such as the first target 102, to provide an echo 104B. The transducer array 110 can be configured to receive a portion of the echo 104B. The analog front end circuit 106 can be configured for processing the resulting transduced echo signal, such as conditioning, delaying, filtering, phase-rotating, or otherwise processing the received echo 104B.

Signal processing can further include converting the received energy from an analog signal representation into a digital representation, such as using one or more of the analog-to-digital converters 108. In an array example, one or more of the bus 112, the A/D converters 108, or the digital logic circuit 114 can include a respective channels corresponding to respective transducers included in the array of transducers 110. For example, a transducer in the array of transducers 110 can be coupled to a respective portion of the analog front end 106, including a respective analog-to-digital converter, or buffered by a respective digital buffer. In an array example, one or more portions of the analog front end 106, the one or more analog-to-digital converters 108, or the digital logic circuit can be commonly-shared between two or more transducers, such as to simplify the construction of an ultrasonic transducer assembly 120, such as multiplexed over time e.g., within a single transmission or across multiple transmissions).

In an example, the storage unit 130 can be included as a portion of a general or special purpose computer, such as the computer system 126. For example, ultrasonic echo information obtained from the ultrasonic transducer assembly 120, and stored on the storage unit 130, such as transferred to the storage unit 130 via a wired or wireless communication link 116C. In an example, the ultrasonic echo information can be processed, such as to reconstruct an image including a representation showing the target 102. Such processing need not occur using the same computer system 126 as can be used to control the transducer assembly 120.

One or more techniques such as included in the examples below can be machine-implemented or computer implemented, such as performed by the system 100 corresponding to instructions stored in one or more of the memory circuit 124 or the storage unit 130, among others. In an example, one or more of the memory circuit 124 or the storage unit 130 can include a processor-readable medium, such as comprising instructions that when performed by the first or second processors 122, 118, cause the processors or system to perform one or more of the techniques included in the examples below.

In an example, the transducer array 110 can be configured to insonify the region of interest 132 using ultrasonic energy, and the region of interest can include a tissue region (e.g., a breast region, a testicular region, or one or more other locations). In such an illustrative tissue imaging example, the target 102 can represent a cyst, or other inhomogeneity in the region of interest 132. In such an illustrative tissue imaging example, reflected energy can include an ultrasonic echo 104B that can be digitized and converted to an echo data set provided to the computer system 126. For example, the computer system 126 can then construct a representation e.g., a C-mode representation or one or more other representations), such as for presentation as an image using the display 128.

In an illustrative example, the first processor circuit 122 can include a cell-phone class "Open Multimedia Application Platform" (OMAP) 3530 microprocessor, such as available from Texas Instruments Inc. (Dallas, Tex., USA). The array 110 can include a 60×60 channel array that can be focused, such as using a 40×40 aperture, such as to provide a frame rate per C-mode slice that increases from 16 Hz using a non-separable DAS approach to 255 Hz for a separable DAS approach, and from 11 Hz for a non-separable DSIQ approach to 193 Hz for a separable DSIQ approach. In this illustrative example, energy usage per frame can reduced from 75 millijoules (mJ) per frame to 4.8 mJ/frame for the non-separable vs. separable DAS approach, and from 107 mJ/frame to 6.3 mJ/frame for the non-separable vs. separable DSIQ approach. Generally, under specified conditions, such separable techniques can also outperform 2D Fast-Fourier-Transform-based (FFT) focusing by a factor of 1.64 at corresponding data sizes. Accordingly, the present inventor has recognized that separable techniques can significantly improve frame rate and battery life for hand-held devices with 2D arrays as compared to using non-separable or exclusively-FFT-based techniques.

Figure 2:
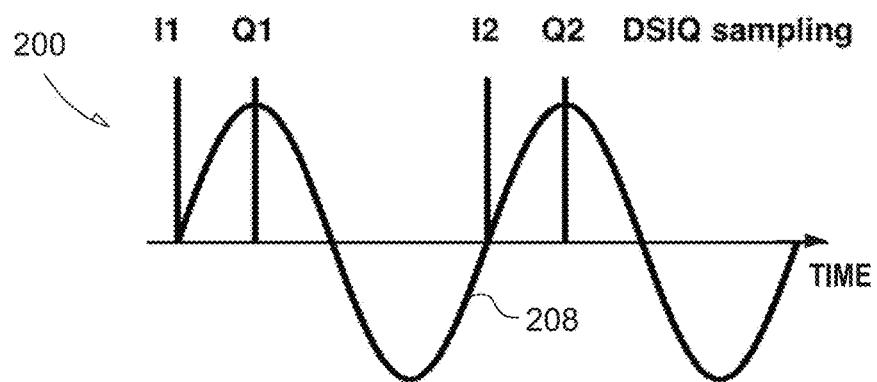
FIG. 2 illustrates generally an example of a technique, such as a method, such as for sampling a time-domain waveform that can approximate a complex representation of the waveform.

FIG. 2 illustrates generally an example of a technique, such as a method 200, of sampling a time-domain waveform 208 that can approximate a complex representation of the waveform 208. Such a waveform 208 can correspond to echo information obtained from one or more ultrasonic transducers included in a 2D array. The present inventor has recognized, among other things, that Direct Sampled In-phase/Quadrature (DSIQ) sampling can be included as a portion of an efficient phase-based focusing technique, such as for constructing a C-mode imaging representation using a portable hand-held 2D array ultrasound system. In a DSIQ sampling technique, one or more pairs of samples, such as including one or more respective pairs comprising a first sample, and a second sample delayed by a quarter period, can be obtained, such as corresponding to a specified depth slice having a round-trip propagation delay corresponding to a time of the first sample (e.g., corresponding to an arrival time at the transducer of the reflected energy from the specified depth). For example, such a DSIQ sampling technique can include, in response to a plane-wave transmit, contemporaneously obtaining samples from a specified group of transducers at a specified time of interest, I1 (e.g., according to a specified imaging depth), then at one or more further delays, such as of one quarter period, Q1, one period, I2, and one-and-a-quarter periods, Q2, of the transmit waveform 208 center frequency, as shown in the example of FIG. 2.

In the illustrative example of FIG. 2, this can provide two pairs of samples per channel that, according to a narrowband assumption, can approximate the real and imaginary parts of a complex demodulated baseband signal, such as for use in phase-rotation-based focusing. One or more other phase-rotation based beamformers can be used. However, the sparse sampling of DSIQ is suited to high-channel count, hand-held imaging systems.

The performance of separable focusing techniques for C-mode imaging can be evaluated by comparison of such separable techniques, such as including a separable delay-and-sum (SDAS) technique or a separable DSIQ focusing (SDF) technique, to corresponding non-separable delay-and-sum (NDAS) and non-separable DSIQ focusing (NDF) techniques. A computation performance of FFT-based 2D-array DSIQ focusing can also be assessed relative to separable DSIQ focusing.

In a 2D array ultrasound system using an NDAS approach, signals from an M×N receive aperture of a larger array, arranged laterally about the projection of the focal point onto the transducer plane, can be delayed and weighted before summing, such as to form a single beamformed output value.

This can be represented in EQNS. (1) through (3) for time-delay focusing at a point at location, $(X, Y, Z_f)$, in space in the region under an array element at a location, $(p, q)$. The expressions $x(i)$ and $y(j)$ can represent coordinates of an aperture element $(i, j)$, 'k' can represent a wavenumber, $2\pi f_{center}/c$, $R_{XY}(i, j)$ can represent a distance from aperture element $(i, j)$ to the focal point, $\tau(i, j)$ can represent an associated propagation time delay, $A(i, j)$ can represent an apodization function over the aperture, and $s(i, j, t-\tau_{XY}(i, j))$ can represent a time signal from aperture element $(i, j)$, such as delayed by $T_{XY}(i, j)$. The summation output $F_{XY}(p, q, t)$ can represent a time series that can be evaluated at t=0, such as after envelope detection or other processing.

In another approach, such as for phase-rotation based focusing, a complex sample can be obtained for respective elements in the focal aperture, $s(i, j)$. A complex weight that can be represent by $C(i, j)$, from EQN. (4), can then be applied, such as incorporating one or more of propagation phase or apodization, such as before summation as in EQN. (5).

$$R_{XY}(i, j) = Z_f + \sqrt{(X - x(i))^2 + (Y - y(j))^2 + Z_f^2} \quad (1)$$

$$\tau_{XY}(i, j) = R_{XY}(i, j)/c \quad (2)$$

$$F_{XY}(p, q, t) = \sum_{i=-(M-1)/2}^{(M-1)/2} \sum_{j=-(N-1)/2}^{(N-1)/2} A(i, j)s(p - i, q - j, t - \tau_{XY}(i, j)) \quad (3)$$

$$C(i, j) = A(i, j)e^{-jkR_{XY}(i,j)} \quad (4)$$

$$F_{XY}(p, q) = \sum_{i=-(M-1)/2}^{(M-1)/2} \sum_{j=-(N-1)/2}^{(N-1)/2} C(i, j)s(p - i, q - j) \quad (5)$$

Figure 3A:
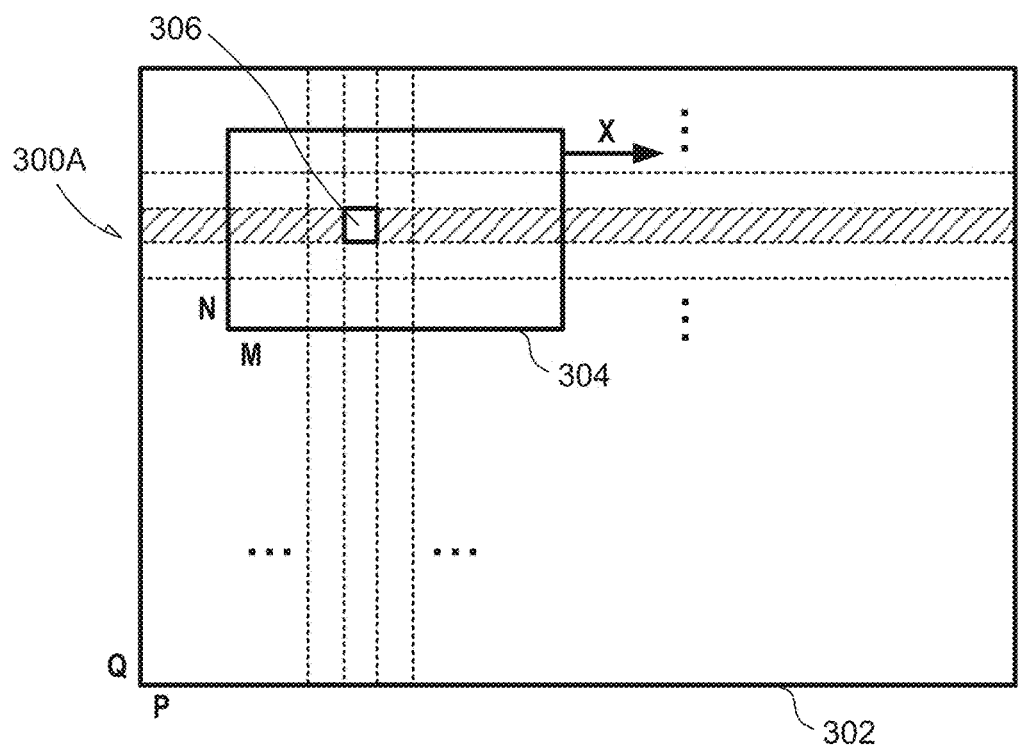
FIG. 3A illustrates generally an example that can include a non-separable 2D focusing technique.

FIG. 3A illustrates generally an example that can include a non-separable 2D focusing technique 300A. In the example of FIG. 3A, an M×N focal aperture 304 can be translated (e.g., such as in a direction, "X") to focus at a series of P points in the azimuthal direction (e.g., as shaded). To focus at one point, such as a specified focusing location 306, can include M times N 'delay' and sum operations, where 'delay' may be a real time delay or a phase-rotation based approximation to a time delay. Aperture apodization can also be applied in each case. To construct a C-mode representation of a specified plane 302 of P×Q focused points can include a product of (MNPQ) delay-and-sum operations. Such an NDAS focusing technique can be interpreted as a spatial filtering or convolution operation. Using EQN. (5), a phase-rotation based technique can be interpreted as a 2D complex convolution operation.

Figure 3B:
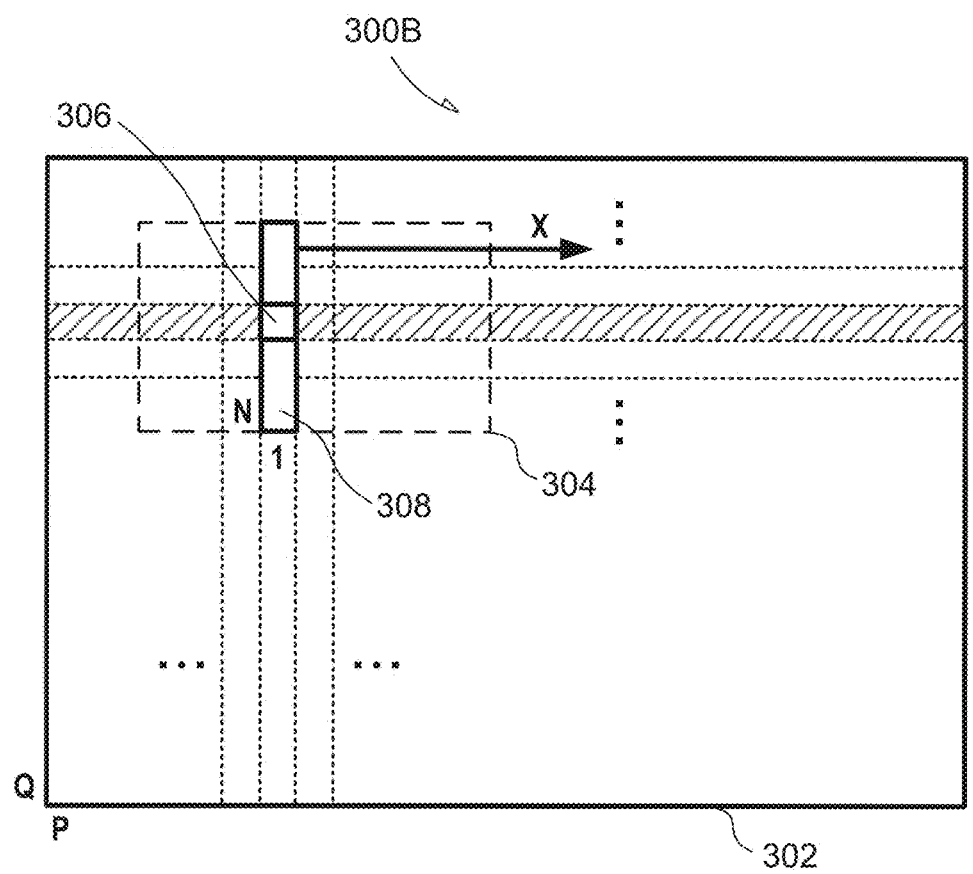
FIGS. 3B and 3C illustrate generally a separable focusing technique, such as including determining a set of first beamformed sums along respective first lines in FIG. 3B, and separately determining a second beamformed sum corresponding to a specified focusing location along a second line, the first and second lines orthogonal to each other on the transducer array.
Figure 3C:
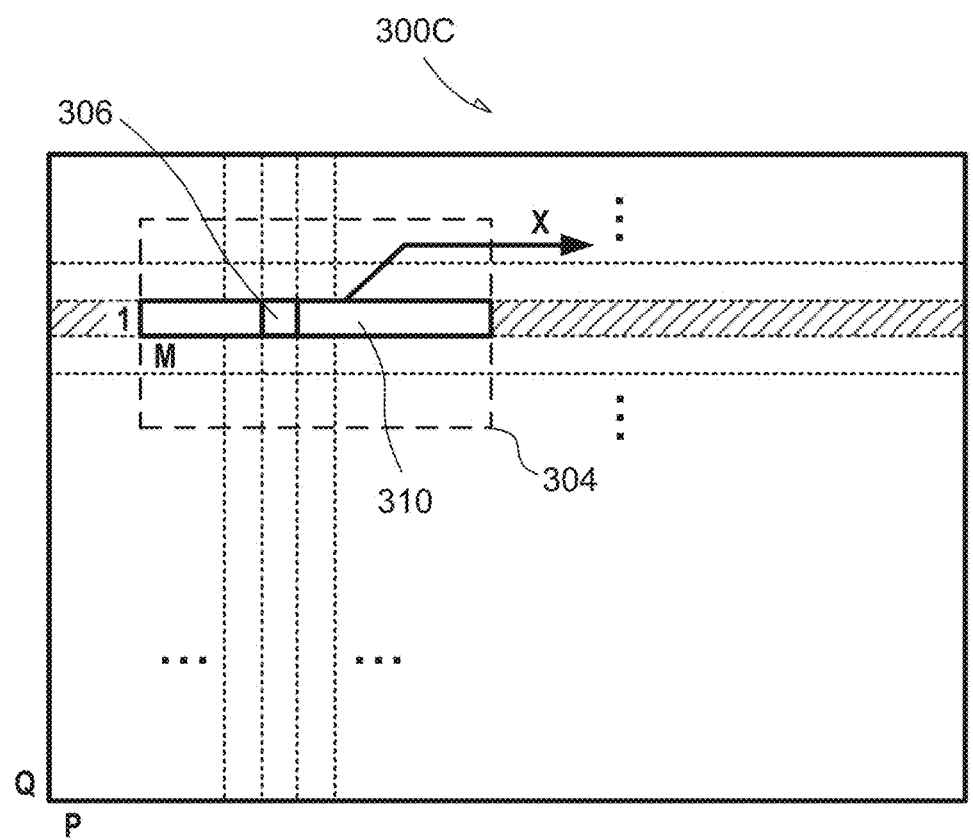

FIGS. 3B and 3C illustrate generally a separable focusing technique, such as including determining a set of first beamformed sums 300B along respective first lines in FIG. 3B, and separately determining a second beamformed sum 300C corresponding to a specified focusing location along a second line, the first and second lines orthogonal to each other on the plane defined by the aperture (e.g., such as corresponding to respective lines of transducers that can be orthogonal to each other in a plane defined by the transducer array).

Separable 2D array can generally include decomposing a propagation distance that can be represented by $R_{XY}(i, j)$ into two components, $R_X(i)$ and $R_Y(j)$, such that $R_{XY}(i, j)$ can be approximately represented by $R_X(i)+R_Y(j)$. Similarly, an apodization weighting $A(i, j)$ can be approximated by a product $A_X(i)A_Y(j)$ Such approximations can reduce a number of delay and weighting operations for an M×N aperture from (MN) in a non-separable example, to (M+N) in a separable example. For example, the M possible unique azimuthal delays or weights for an element can be re-used when the element is at N different elevational positions in an aperture and vice versa. The terms elevation and azimuth can refer to respective orthogonal dimensions in a plane defined by the transducer array or aperture, as compared to a depth dimension, which can represent a distance in a direction orthogonal to the plane defined by the transducer array or aperture.

The separable techniques represented in FIGS. 3B and 3C can include an M×N aperture 304, such as can be used to focus at a line of P points in the azimuthal direction (e.g., as shaded), such as can repeated for each of Q elevational lines to form a full P×Q representation 302 (e.g., a C-mode imaging representation of a specified plane within tissue).

For example, in FIG. 3B, a line of P partially focused outputs are formed by summing over a 1×N elevational aperture 308 with delays corresponding to $R_Y(j)$ and weights of $B(j)$, as the aperture translates to cover P respective azimuthal focusing locations such as a specified location 306, such as to provide respective first partial beamforming sums.

In an example, such as after determining the first partial beamforming sums as shown in the example of FIG. 3B for respective azimuthal focusing locations, an M×1 aperture 310, such as using one or more of delays corresponding to $R_X(i)$ or weights of $A(i)$, can be used to form azimuthal sums (e.g., separate second sums) as the aperture translates over P azimuthal locations, as shown in the example of FIG. 3C.

For example, a first partial sum of N delayed and weighted values from the example of FIG. 3B can be re-used M times in a second sum. In this manner, a line of P focused points can be determined for Q similar lines at different elevational positions, and a corresponding total number of delay, weight, and accumulate operations for such a separable focusing process can be represented by PQ(M+N). Such a technique can include separately determining first sums corresponding to first lines of transducers (or elements in the aperture) and re-using such sums in determining a second sum corresponding to a second line of transducers (or elements in the aperture), orthogonal to the respective first lines, Such a separable technique can reduce a computational cost by a factor (M+N)/MN as compared to a non-separable technique.

$$r_{XY} = \sqrt{Z_f^2 + \Delta X^2 + \Delta Y^2} = Z_f \sqrt{1 + \frac{\Delta X^2}{Z_f^2} + \frac{\Delta Y^2}{Z_f^2}} \quad (6)$$

$$\sqrt{1+b} = 1 + \frac{1}{2}b - \frac{1}{8}b^2 + \frac{1}{16}b^3 \ldots b = \frac{\Delta X^2}{Z_f^2} + \frac{\Delta Y^2}{Z_f^2} \quad (7)$$

$$r_{XY} = Z_f\left(1 + \frac{1}{2}\left(\frac{\Delta X^2}{Z_f^2} + \frac{\Delta Y^2}{Z_f^2}\right) - \frac{1}{8}\left(\frac{\Delta X^2}{Z_f^2} + \frac{\Delta Y^2}{Z_f^2}\right)^2 \ldots\right) \quad (8)$$

$$r_X = Z_f\left(1 + \frac{1}{2}\left(\frac{\Delta X^2}{Z_f^2}\right) - \frac{1}{8}\left(\frac{\Delta X^2}{Z_f^2}\right)^2 \ldots\right) \quad (9)$$

$$r_Y = Z_f\left(1 + \frac{1}{2}\left(\frac{\Delta Y^2}{Z_f^2}\right) - \frac{1}{8}\left(\frac{\Delta Y^2}{Z_f^2}\right)^2 \ldots\right) \quad (10)$$

The geometric delay $R_{XY}(i, j)$ from EQN. (1) can be decomposed into the separable components represented by $R_X(i)$ and $R_Y(j)$, and the rightmost term of $R_{XY}(i, j)$ can be rewritten as $r_{XY}$ in EQN. (6), such as where the x- and y-dimension differences can be represented by $\Delta X$ and $\Delta Y$ respectively. In an example, a Taylor series expansion of EQN. (6) can be represented by EQNS. (7) and (8). The first two terms of such an expansion can be treated as a Fresnel approximation, and in EQNS. (9) and (10), $r_X$ and $r_Y$ can represent the Taylor expansions of EQN. (6) but with $\Delta Y$ and $\Delta X$ set to zero, respectively.

Such a sum of three-term Taylor expansions of $r_X$ and $T_Y$ can be approximately the same as a three-term expansion of $r_{XY}$ except for an additional constant $Z_f$ and a non-separable X-Y component in the third term of $r_{XY}$. Accordingly, $R_{XY}(i,j)$ can approximate $R_X(i)+R_Y(j)$ such as using EQNS. (11) and (12), such as where a $-Z_f$ term in $R_Y(j)$ can be used to cancel an extra constant that would otherwise appear in the sum $R_X(i)+R_Y(j)$. EQN. (13) can represent resulting azimuthal and elevational propagation time delays. $T_X(i)$ and $t_Y(j)$, which can similarly satisfy that $t_{XY}(i, j)$ can approximate $t_X(i)+\tau_Y(j)$.

$$R_X(i) = Z_f + \sqrt{(X-x(i))^2 + Z_f^2} \quad (11)$$

$$R_Y(j) = -Z_f + \sqrt{Y-y(j))^2 + Z_f^2} \quad (12)$$

$$\tau_X(i) = R_X(i)/c, \; \tau_Y(j) = R_Y(j)/c \quad (13)$$

Delay, weight, and summation steps of a separable focusing technique can be represented for a delay-and-sum implementation in EQNS. (14) and (15). The summation output $F_{XY}(p, q, t)$ can represent a time series that can be evaluated, such as at t=0 after envelope detection. In another approach, such as when a phase-rotation based focusing technique is used, two separable focusing steps can be represented in EQNS. (16) and (17), including using complex-valued multiplications (e.g., including both magnitude and phase information) rather than real-valued time delays.

$$F_X(p, q, t) = \sum_{i=-(M-1)/2}^{(M-1)/2} A_X(i)s(p - i, q, t - \tau_X(i)) \quad (14)$$

$$F_{XY}(p, q, t) = \sum_{j=-(N-1)/2}^{(N-1)/2} A_Y(j)F_X(p, q - j, t - \tau_Y(j)) \quad (15)$$

$$F_X(p, q) = \sum_{i=-(M-1)/2}^{(M-1)/2} A_X(i)e^{-jkR_X(i)}s(p - i, q) \quad (16)$$

$$F_{XY}(p, q) = \sum_{j=-(N-1)/2}^{(N-1)/2} A_Y(j)e^{-jkR_Y(j)}F_X(p, q - j) \quad (17)$$

Respective 2D summation over a focal aperture 304 as it shifts in a 2D plane across the sample data can represent a convolution. For example, an N×N sized 2D convolution can be calculated using the convolution theorem, 2D FFTs and corresponding Inverse FFTs (IFFTs). Respective 2D FFTs can be determined in $O(N^2 \log(N))$ time, such as corresponding to "N" 1D FFTs for respective X and Y dimensions, such as consuming a duration of $O(N \log (N))$ individually. However, zero-padding is generally used to avoid cyclic convolution issues, and such a dual domain (time domain and frequency domain) data representation increases memory requirements, such as precluding implementation of such FFT-based techniques using L1 cache capabilities of a processor circuit, alone, and generally including frequent accessing of slower main memory. In addition, if fixed-point arithmetic is used, FFT-based convolution can introduce significant rounding errors that increase with FFT length.

Examples Including Simulated and
Experimentally-Obtained Results

In various illustrative examples, experimentally obtained and simulated data can use the array parameters of TABLE 1.

TABLE 1

An illustrative example of ultrasound transducer array parameters.

| Property | Value | Units |
|---|---|---|
| Array Size | 60 × 60 | Element |
| Pitch | 300 | μm |
| Center Frequency | 5 | MHz |
| Cycles (DSIQ) | 4 | N/A |
| Cycles (DAS) | 2 | N/A |

Non-separable delay-and-sum (NDAS) and separable delay-and-sum (SDAS) focusing techniques can be implemented at least in part using MATLAB (Mathworks, Natick, Mass.). In an example, two different kinds of time-delay interpolation can be used for such techniques, such as an 8-sample Hamming-windowed sinc function, or a cubic B-spline based method. Generally, cubic B-spline interpolation can be implemented by operating a 2-tap Infinite Impulse Response (IIR) filter up, then down respective receive channel time-series', such as before application of a 4-tap Finite Impulse Response (FIR) filter for respective individual interpolations Because there can be many more time-delay operations than receive channels, to a limiting extent, the B-spline technique can be approximately twice as fast as an 8-tap windowed sinc operation, with a corresponding interpolation error reduced by 3.5 decibels (dB) to 5.5 dB.

In an illustrative example, such as for NDAS focusing, a 2D time delay profile from EQN. (3) can be used to create an N×N×L convolution kernel, with respective N×N vertical time series' implementing a time delay, such as using windowed sinc (L=8) or B-spline interpolation (L=4), with an integer sample offset. Such a kernel can then be used in a spatially variant 3D convolution with volume data from a 60×60 array to produce focused RF output.

In an illustrative example, such as for SDAS focusing, a 1×N×L azimuth-focused kernel and an N×1×L elevation-focused kernel can be used, such as according to EQNS. (11) through (13), and convolved together to make an effective kernel for focusing similar to the NDAS illustrative example.

Non-separable DSIQ focusing (NDF) and separable DSIQ focusing (SDF) techniques can also be implemented in MATLAB (Mathworks, Natick, Mass.), such as operating on 4 real samples per channel to obtain an approximation of complex samples. For example, such samples can be obtained at specified time intervals, such as can be represented by $s_1 = t_0$, $s_2 = t_0 + \lambda/4$, $s_3 = t_0 + \lambda$, $s_4 = t_0 + 5\lambda/4$, with $\lambda = f_c/c$, and $t_0$ can represent the round-trip propagation time from the array to a specified focal depth. The first two samples per element, separated by a quarter period, can be treated respectively as the real and imaginary parts of a first complex sample (e.g., approximating a complex sample obtained such as using coherent demodulation). The next two samples can similarly approximate a second complex sample. One or more specified time-delays can then be implemented in the frequency domain, such as using a weighted phase rotation of the respective two complex samples per respective channel.

A respective set of first complex samples from respective channels can be focused separately from a set of second complex samples, and the results can be added. In this manner, respective independent complex focusing kernels can be used respectively for the first or second complex sample data sets, such as taking into account a closeness to a geometric waveform center in time with respect to the first or second complex samples. A weighting function can be used for respective aperture elements, (i, j), such as to bias the final output towards a complex sample closest to an ideal or specified time delay.

For example, a Gaussian function, including a full-width half maximum (FWHM) about equal to a separation of the two complex samples can be used to change weighting smoothly while biasing strongly towards the nearest complex sample. This can be represented in EQN. (18), such as where $w_{s(i,j)}$ can represent a complex sample weight, and $t_s$ can represent a complex sample time, $\tau(i,j)$ can represent a geometric target time delay for a corresponding aperture element, (i, j) and k can represent a constant chosen to achieve the specified FWHM for the weighting.

$$w_s(i,j) = e^{-k(t_s - \tau(i,j))^2}, \quad k = -4 \ln(0.5) f_0^2/\lambda^2 \tag{18}$$

In illustrative examples including simulations or experimentally-obtained results, an N×N focusing aperture can be assumed, based on f-number. In the example of NDF, for the two complex samples, respective N×N arrays of complex focusing coefficients can be calculated for a specified focal depth using EQNS. (1), (4), and (5), including radially symmetric apodization and per-element aperture weighting that can be represented by EQN. (18).

In an illustrative example, the MATLAB function 'conv2' can be used to perform 2D complex convolution in-place using double-precision floating point arithmetic. The phase of the non-separable 2D DSIQ focusing aperture can be used as a reference phase for calculation of root-mean-square phase error of the separable focusing techniques. Apodization-weighted RMS phase errors can be calculated to give an indication of phase error significance, such as taking into account aperture shading.

For SDF focusing, azimuth-focused and elevation-focused focusing vectors can be produced, such as including dimensions 1×N and N×1 respectively, such as represented by EQNS. (11) through (13), and such as using the same apodization window used for both $A_X(i)$ and $A_Y(j)$. The two 1D focusing vectors can be convolved together to form an N×N convolution kernel that can represent an outer product, such as can be applied independently to the first and second set of complex samples before combination into a final image representation. For the SDF technique, the weighting represented by EQN. (18) can be applied in the x- and y-dimensions, such as producing an N×N product aperture weight as used for NDF.

In an illustrative example, simulation of one or more techniques can be performed, at least in part, such as using FIELD II software, using parameters such as shown in TABLE 1, such as including 2×2 modeled transducer elements per physical transducer element and using a Gaussian-windowed transmit pulse including a specified bandwidth. In FIELD II, a sample rate of 128 times the center frequency can be used, such as to avoid artifacts. An output of such simulation can be downsampled to about 40 MHz before beamforming, such as to simulate performance of a practically-achievable hardware system. To compare separable beamformer imaging performance to non-separable equivalents, simulated PSFs and beamplots, plus simulated and experimental anechoic cyst images can be produced. For the anechoic cyst images, contrast-to-noise ratios (CNRs) can be calculated such as using EQN. (19), where μ and σ can represent the log-scale mean and standard deviations of the image in specified lesion or background areas as subscripted.

$$CNR = (\mu_{lesion} - \mu_{bgnd})/(\sigma_{lesion} + \sigma_{bgnd})^{1/2} \tag{19}$$

Experimentally-obtained information can be obtained such using a hardware configuration discussed generally in various examples herein, such as the example of FIG. 1, or the example of U.S. Pat. No. 7,699,776, which is hereby incorporated herein by reference in its entirety. For example, a portable, battery operated system can include an integrated 2D transducer, such as including hardware or acquisition parameters as in the example of TABLE 1. Such an assembly can weigh less than about 170 grams, for example, and can include one or more respective custom front-end ICs flip-chip attached to a 2D transducer array such as to obtain ultrasound echo information from respective elements contemporaneously during a specified time interval after a transmit event.

For experimentally-obtained information, a 4-cycle, 5 MHz transmit pulse can be used. Such a pulse can be followed by a capture of 4 samples per element at specified durations (e.g., for a DSIQ sampling technique), such as using a 40 MHz sample clock. Images corresponding to a specified plane in a tissue region (or phantom) can be obtained such as by aggregating information from respective C-mode representations. For example, experimentally-obtained B-mode images can be constructed, such as stacking respective slices from successively acquired C-mode image planes, corresponding to different imaging depths. In this manner, echo information corresponding to a specified volumetric region of tissue can be obtained.

A tissue mimicking near-field ultrasound phantom, such as a CIRS Model 050 (CMS, Norfolk, Va., USA), such as including a 10 mm diameter anechoic cylinder at a depth of 15 mm, can be used as a target for the experimentally-obtained information.

Computation time for performing respective non-separable or separable versions of delay-and-sum (NDAS, SDAS) and DSIQ focusing (NDF, SDF) can be measured for a variety of aperture sizes, such as using the OMAP 3530 "smart phone"-oriented processor circuit, such as in the example of the first column of TABLE 2, or discussed above with reference to the example of FIG. 1. The energy cost of computation can be determined using an integration of measured current consumption of the OMAP processor and associated Power Management Integrated Circuit (PMIC), such as using a supply voltage of 3.3 Volts DC (VDC).

For experimentally-obtained information using the OMAP processor circuit, one or more techniques can be implemented in the programming language, such as using 16-bit signed integer data types, compiled with the GNU 'gcc' compiler using an '−O3' code optimization level, such as with and without inner loop optimization for use of single-instruction multiple-data (SIMD) assembly instructions. In an illustrative example, such SIMD instructions can be used, for example, to perform four multiply-accumulate operations in parallel. For experimentally-obtained information, a reported "computation time" can represent a duration to focus (e.g., determine) a single C-mode slice of a volume-focused image.

For illustrative examples including delay-and-sum focusing techniques using cubic B-spline interpolation, this can represent a time duration to perform 4 separate scalar 2D convolutions of a 60×60 array with an N×N kernel. For illustrative examples including DSIQ-based focusing, such "computation time" can represent a time duration to perform 2 complex 2D convolutions of a 60×60 array with an N×N kernel. Such timed computation can be averaged over 100 runs, such as alternating between two input data sets to obtain cache usage indicative of a realistic use case.

In another illustrative example, the performance of separable 2D focusing using convolution can be compared with FFT-based 2D convolution, such as implemented using MATLAB (e.g., using 'fft2' and 'conv2' built-in functions), such as operating on double precision complex floating-point data on an Intel Core i5 laptop processor circuit (e.g., as shown in the example of the second column of TABLE 2).

TABLE 2

An illustrative example of processor circuits that can be used to implement one or more separable beamforming techniques.

| | Processor | |
|---|---|---|
| | OMAP3530 | Core i5 |
| Manufacturer | Texas Instruments | Intel |
| System | Gumstix Overo (www.gumstix.org) | 15" Macbook Pro (Apple, Inc. (Cupertino, CA, USA) |
| Architecture | ARM | IA32/64 |
| Family/Variant | Cortex A8 | Arrandale (mobile) |
| Cores | ARM + C64 DSP (unused) | 2 |
| Processor Clock | 720 MHz | 2.4 GHz |
| L1 memory | 16 KB(I) + 16 KB(D) | 32 KB(I) + 32 KB(D)/core |
| L2 memory | 256 KB | 256 KB/core |
| L3 memory | N/A | 3 MB |
| Main Memory Access | 166 MHz/32 bit | 1066 MHz/64 bit |
| Typical Power | 1 W | 35 W (Thermal Specification) |

Figure 4B:
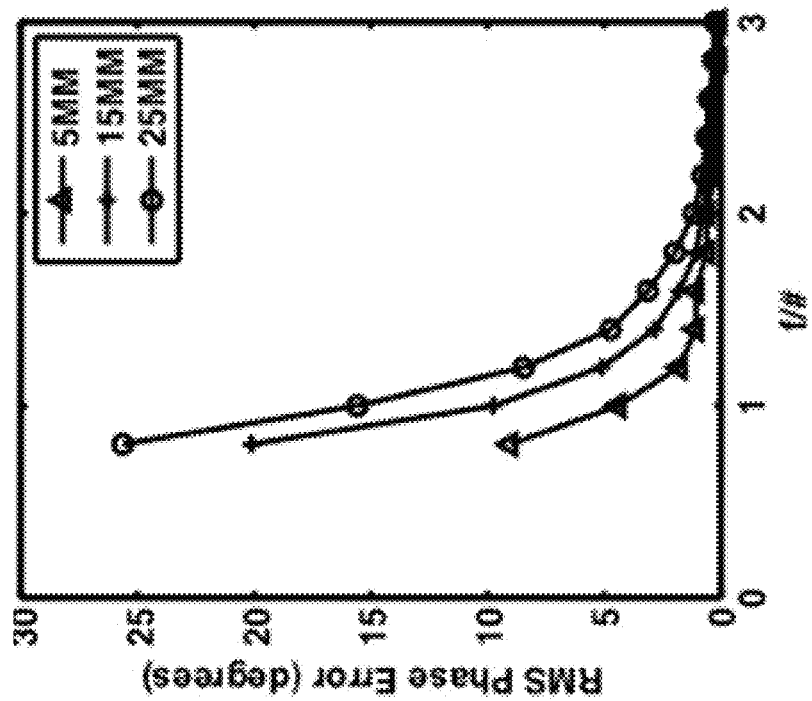
FIGS. 4A and 4B illustrate generally illustrative examples of simulated root-mean-square (RMS) phase errors corresponding to respective focal depths for an unweighted SDAS technique in FIG. 4A, and an apodization-weighted SDAS technique in FIG. 4B.
Figure 4A:
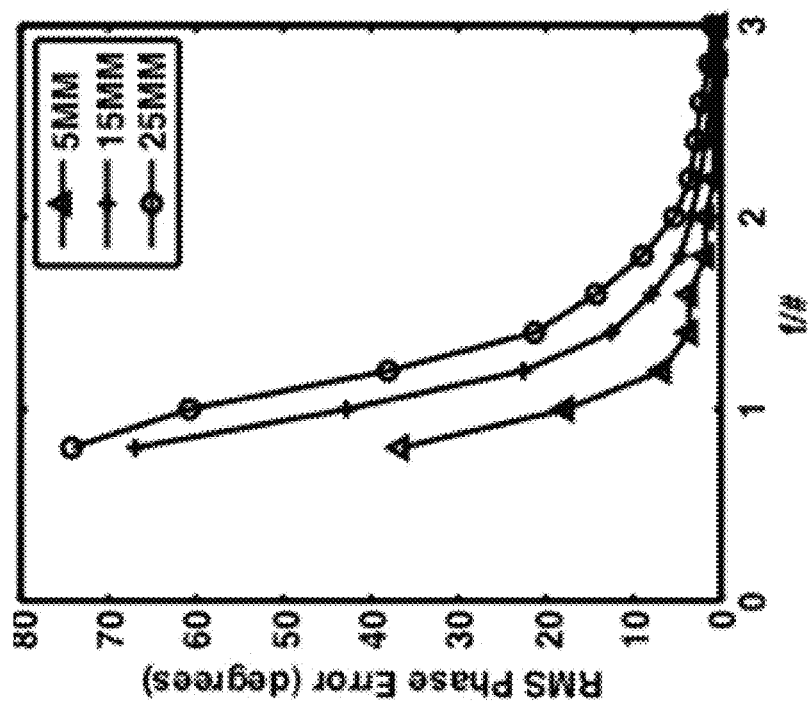

FIGS. 4A and 4B illustrate generally illustrative examples of simulated root-mean-square (RMS) phase errors corresponding to respective focal depths for an unweighted SDAS technique in FIG. 4A, and an apodization-weighted SDAS technique in FIG. 4B. Such phase errors are simulated for focal depths of 5 millimeters (mm), 15 mm and 25 mm, and a varying f-numb (f/#) from 0.8 to 3.0. Generally, as shown in the illustrative example of FIG. 4B, apodization-weighted RMS phase errors can be less than about 1/32 cycle for f/# greater than about 1.0 and a focal depth less than or equal to about 15 mm.

FIGS. 5A and 5B illustrate generally illustrative examples showing an interpolation error in respective simulated beamplots for an NDAS technique in FIG. 5A and an SDAS technique in FIG. 5B, such as focused at a depth of about 15 mm, with f/#=1.4, and such as using a windowed-sinc or B-spline based interpolation technique.

Figure 6:
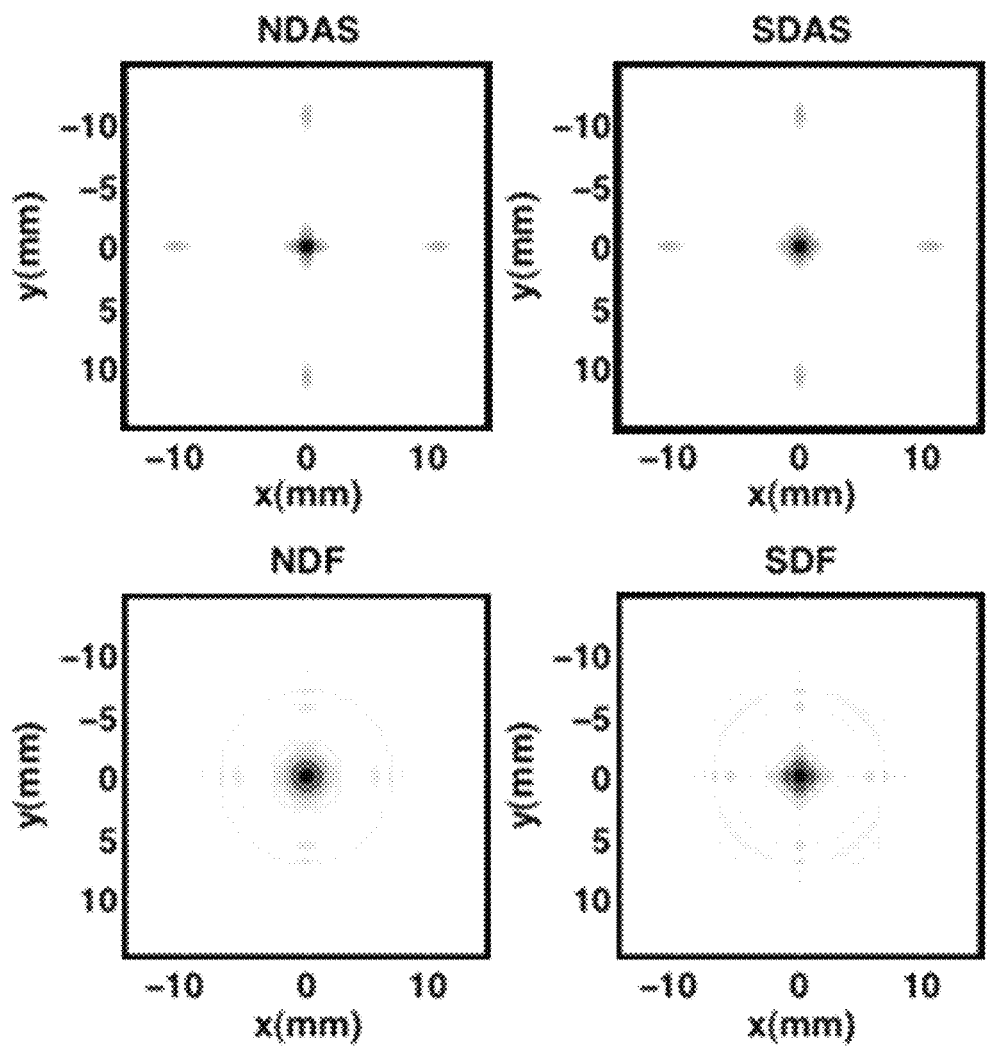
FIG. 6 illustrates generally an illustrative example of respective simulated Point Spread Functions (PSFs) corresponding to NDAS, SDAS, NDF, and SDF beamforming techniques.

FIG. 6 illustrates generally an illustrative example of respective simulated Point Spread Functions (PSFs) corresponding to NDAS, SDAS, NDF, and SDF beamforming techniques. Such elevational-azimuthal PSFs can be obtained respectively for respective non-separable or separable versions of delay-and-sum (NDAS, SDAS) and DSIQ focusing (NDF, SDF), such as using f/#=1.4, a focal depth of 15 mm, a 65 dB logarithmic display range, a2-cycle transmit for DAS examples, or a4-cycle transmit for DSIQ examples.

Figure 7A:
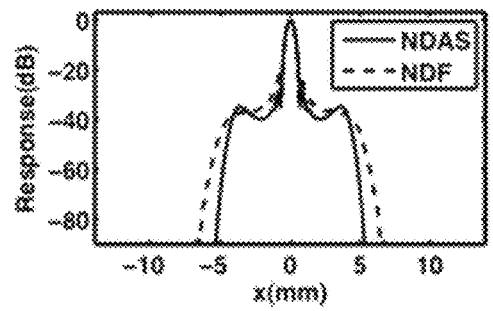
FIGS. 7A through 7F illustrate generally illustrative examples of respective simulated beamplots corresponding to NDAS, SDAS, NDF, and SDF beamforming techniques, such as can be simulated for various specified focusing depths.
Figure 7B:
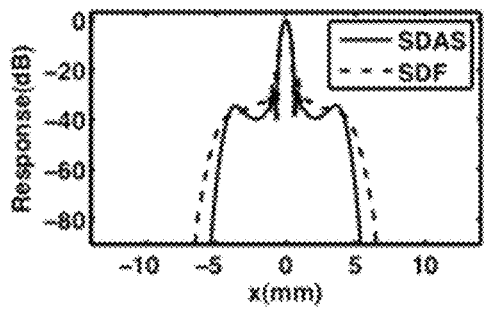
Figure 7C:
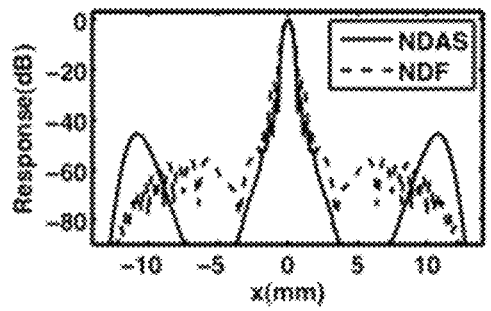
Figure 7D:
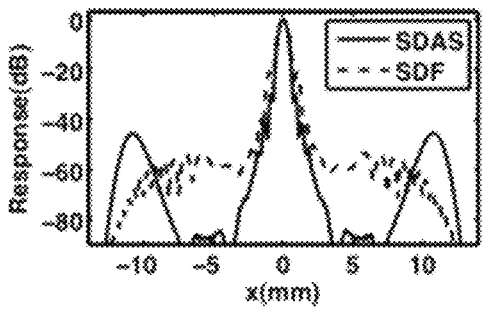
Figure 7E:
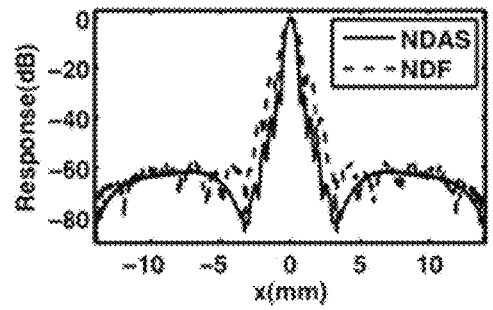
Figure 7F:
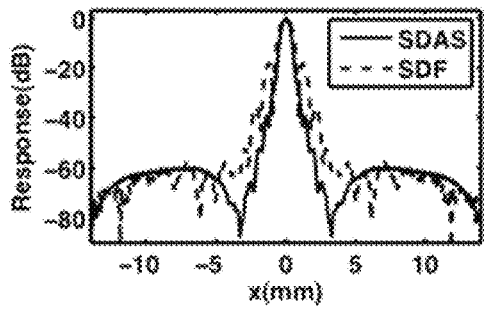
Figure 10A:
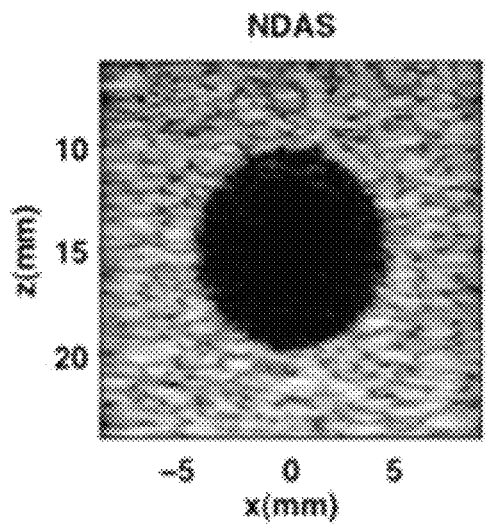
FIGS. 10A through 10D illustrate generally an illustrative example of a comparison between simulated B-mode slices that can be obtained corresponding to NDAS, SDAS, NDF, and SDF beamforming techniques, such as constructed from C-mode image slices of various depths similar to the C-mode image slice of the illustrative examples of FIGS. 9A through 9F.
Figure 10B:
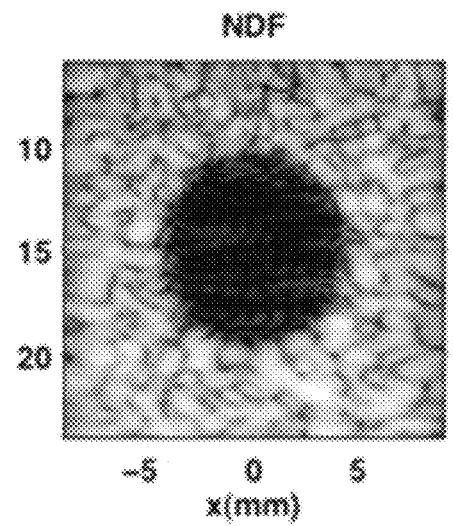
Figure 10C:
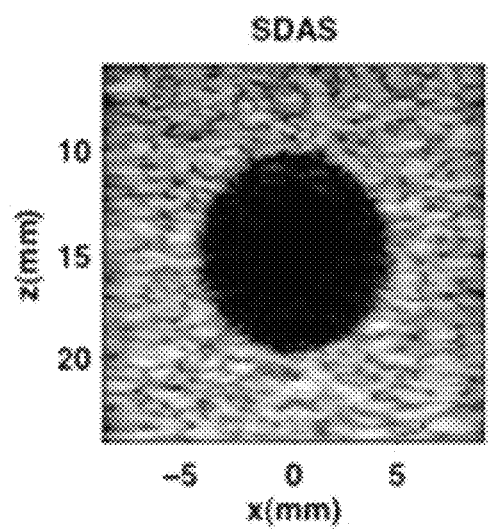
Figure 10D:
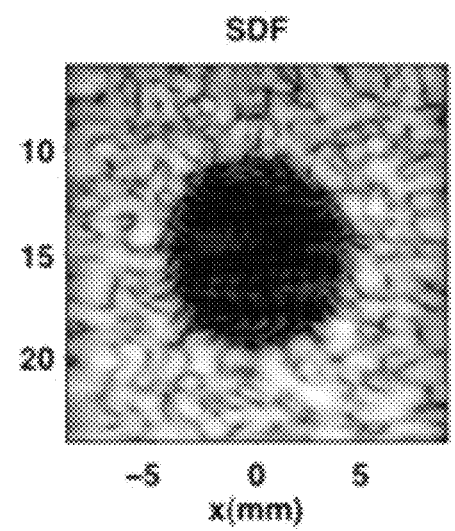

FIGS. 7A through 7F illustrate generally illustrative examples of respective simulated beamplats corresponding to NDAS, SDAS, NDF, and SDF beamforming techniques, such as can be simulated for various focusing depths. FIGS. 7A and 7B include simulation of beamplots that can be obtained corresponding to f/#=1.4 and a focal depth of 5 mm. FIGS. 7C and 7D include simulation of beamplots that can be obtained corresponding to f/#=1.4 and a focal depth of 15 mm. FIGS. 7E and 7F include simulation of beamplots that can be obtained corresponding to f/#=1.4 and a focal depth of 25 mm.

FIGS. 8A through 8I illustrate generally illustrative examples such as can include simulated 2D PSFs for NDAS, SDAS and SDF focusing techniques, under more difficult imaging conditions including low f-number, shallow focal depth, and increased excitation pulse frequency. For example, FIGS. 8A through 8C illustrate simulated PSFs that can be obtained, such as for f/#=0.8, focal depth=5 mm, and center frequency=5 MHz.

FIGS. 8D through 8F illustrate simulated PSFs that can be obtained, such as for f/#=1.0, focal depth=10 mm, center frequency=5 MHz. FIGS. 8G through 8I illustrate simulated PSFs that can be obtained, such as for f/#=1.4 focal depth=15 mm, center frequency=7 MHz.

FIGS. 9A through 9F illustrate generally an illustrative example of a comparison between simulated C-mode images corresponding to NDAS, SDAS, NDF, and SDF beamforming techniques that can be obtained, such as using FIELD II including an simulated anechoic cyst phantom. FIGS. 9A and 9B include respective illustrative examples of C-mode representations of an anechoic cyst that can be simulated using an NDAS beamforming technique in FIG. 9A, or an NDF beamforming technique in FIG. 9B. FIG. 9C illustrates generally an RMS value profile that can be simulated over the y-dimensions of FIGS. 9A and 9B respectively.

FIGS. 9D and 9E include respective illustrative examples of C-mode representations of an anechoic cyst that can be simulated using an SDAS beamforming technique in FIG. 9D, or an SDF beamforming technique in FIG. 9E. FIG. 9F illustrates generally and RMS value profile that can be simulated over the y-dimensions of FIGS. 9D and 9E respectively.

In the illustrative examples of FIGS. 9A through 9F, the anechoic cyst can be simulated to include a 10-mm diameter at a depth of about 15 mm, and the C-mode representations can be obtained using respective beamformers include f#=1.4, a focal depth of about 15 mm, and a 50 dB logarithmic display range. White rectangles can represent areas used to estimate Contrast-to-Noise Ratios (CNRs). Using the C-mode slice at the anechoic cylinder center, contrast-to-noise ratio (CNR) were calculated for the illustrative examples of NDAS, SDAS, SDF and NDF focusing, shown in FIGS. 9A through 9E, giving values of about 4.06 dB, about 4.02 dB, about 3.96 dB and about 3.91 dB respectively. In another illustrative example, simulated NDAS and SDAS cysts, using a 4-cycle transmit pulse, can provide estimated CNRs of 3.64 dB and 3.53 dB, reflecting that DAS can provide worse contrast than DSIQ, such as when using a non-ideal 4-cycle pulse.

FIGS. 10A through 10D illustrate generally an illustrative example of a comparison between simulated B-mode slices that can be obtained corresponding to NDAS, SDAS, NDF, and SDF beamforming techniques, such as constructed from C-mode image slices of various depths similar to the C-mode image slice of the illustrative examples of FIGS. 9A through 9F, but using a 35 dB logarithmic display range and a 4-cycle transmit pulse.

FIGS. 11A through 11F illustrate generally an illustrative example of a comparison between experimentally-obtained C-mode image slices corresponding to NDAS, SDAS, NDF, and SDF beamforming techniques. Experimental volume data can be obtained from a hand-held system including a 60×60, such as discussed in other examples, such as positioned over a 10 mm diameter anechoic cylinder at a depth of 15 mm in a CIRS phantom. As in the examples of FIGS. 9A through 9F, white rectangles can represent areas used to estimate Contrast-to-Noise Ratios (CNRs). Using the C-mode slice at the anechoic cylinder center, contrast-to-noise ratio (CNR) were estimated for the experimentally-obtained information. Corresponding CNR values were about 2.06 dB, about 2.03 dB, about 2.40 dB and about 2.31 dB respectively.

FIGS. 12A and 12B illustrate generally an illustrative example of a comparison of attainable frame-rates versus an aperture dimension, such as can be obtained for various beamforming techniques. The execution times of NDAS, SDAS, NDF and SDF can be compared, such as using the two different hardware platforms of the example of TABLE 2. FIG. 12A illustrates generally C-mode imaging frame rates experimentally achieved, such as by 'C' implementations of the beamforming techniques including inner-loop SIMD optimization on the OMAP 3530 processor. In the illustrative example of FIG. 12A, SDAS and NDAS frame-refresh rates can achieve 254.8 Hz and 16.3 Hz, such as for 40×40 apertures, corresponding to an acceleration factor of about 15.6 times by using the separable technique versus a non-separable technique.

In the illustrative example of FIG. 12A, SDF and NDF frame-refresh rates can achieve 192.8 Hz and 11.39 Hz, corresponding to an acceleration of 16.9 times. FIG. 12B illustrates generally an illustrative example of how the performance of NDF, SDF and 2D FFT-based focusing techniques compare, such as when implemented in MAT-LAB on a Core i5 processor. Compared to the 2D FFT method for aperture sizes of 20×20 and 40×40, the SDF algorithm can achieve acceleration of 2.12 and 1.64 respectively.

The NDAS, SDAS, NDF and SDF techniques can provide estimated energy costs of about 75.0 mJ/frame, 4.8 mJ/frame, 107.2 mJ/frame and 6.3 mJ/frame respectively, such as when using a 40×40 focusing aperture, and implemented in 'C' with inner-loop SIMD optimizations on the OMAP hardware platform.

Figure 13:
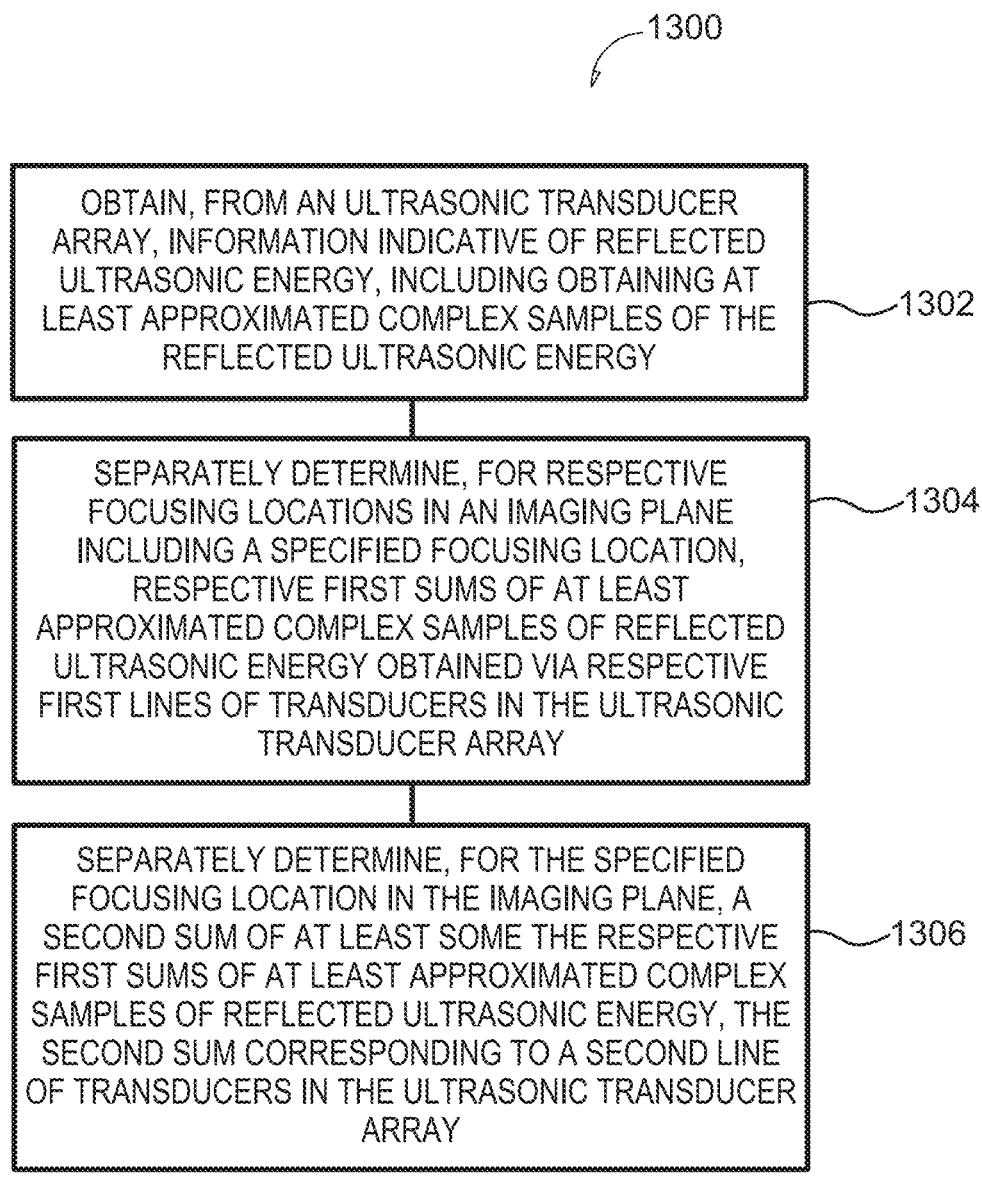
FIG. 13 illustrates generally a technique, such as a method, that can include a separable beamforming technique.

FIG. 13 illustrates generally a technique, such as a method, that can include a separable beamforming technique 1300. At 1302, the technique 1300 can include obtaining, from an ultrasonic transducer array, information indicative of ultrasonic energy reflected from a tissue region. Such information can be obtained such as using a complex sampling technique (e.g., coherent demodulation), or a using one or more techniques to provide at least approximated complex samples, such as a DSIQ sampling technique. The technique 1300 can include applying a specified phase rotation to at least some of the complex samples. The ultrasonic array can include an array defining a two dimensional plane, such as included as a portion of a hand-held apparatus or other system, such as described in the examples above or below.

The technique 1300 can include constructing a representation of a portion of an insonified tissue region, such as a representation of a specified plane of the tissue region (e.g., a C-mode representation, or other plane). Such construction can include, at 1304, separately determining, for respective focusing locations, respective first sums of at least approximated complex samples of reflected ultrasonic energy obtained via respective first lines of transducers in the ultrasonic transducer array, the at least approximated complex samples obtained via respective first lines of transducers corresponding to respective orthogonal projections of the respective focusing locations in the imaging plane onto the respective first lines in the transducer plane.

Such construction can include, at 1306, separately determining, for the specified focusing location in the imaging plane, a second sum of at least sonic the respective first sums of at least approximated complex samples of reflected ultrasonic energy, the second sum corresponding to a second line of transducers in the ultrasonic transducer array. The second line of transducers can be aligned along an axis different from an axis of the respective first lines in the transducer plane (e.g., an orthogonal axis) and corresponding to the orthogonal projection of the specified focusing location in the imaging plane onto the transducer plane.

Separable 2D beamforming can be useful if imaging performance is not significantly degraded as compared to other techniques. The illustrative examples of FIGS. 4A and 4B generally indicate that the RMS phase errors due to separable focusing are much lower when weighted by the aperture apodization function, but increase dramatically for f-numbers lower than about 1.4. In practice, the angular sensitivity of individual elements can deter use of f-numbers below 1.0. In an illustrative example, such as for an operating region of f/# greater than equal to about 1.4, focal depth less than or equal to about 25 mm, a weighted RMS phase error can be less than 5 degrees, which is believed not to have a significant impact on focusing quality.

Generally, delays applied first in the X-direction, then the Y-direction, may introduce cumulative errors. Windowed-sine time delay interpolation with 8 taps has been shown in FIGS. 5A and 5B can introduce significant beamplot degradation for separable delay-and-sum focusing. In contrast, the present inventor has recognized, among other things, that cubic B-spline interpolation may introduce only minimal degradation, and can also be nominally twice as fast as 8-tap sine interpolation.

The simulated beamplots and PSFs represented in FIG. 6 and FIGS. 7A through 7F generally indicate that separable versions of delay-and-sum and DSIQ focusing can suffer minimal degradation over non-separable focusing. Using a separable technique, simulated cyst CNR can be reduced from about 4.06 dB to 4.02 dB for 2-cycle transmit delay-and-sum, and from about 3.96 dB to about 3.91 dB for 4-cycle transmit DSIQ. Such reductions can represent a very minor, perhaps even imperceptible, contrast reduction while still providing significant computational or power savings. Additionally, a difference between delay-and-sum and DSIQ contrast can be similarly minor. For example, application of appropriate weightings to the two DSIQ complex samples can significantly reduce the PSF energy outside the mainlobe and side lobes, approaching delay-and-sum contrast, but with a slightly wider mainlobe and slightly reduced resolution.

Experimentally-obtained cyst CNR values generally indicate that separable techniques can provide contrast comparable to non-separable techniques. It is believed that a difference in experimental CNR magnitude compared to simulations can be attributed to the presence of distributed phase deficiencies (conservatively estimated at about 14 nanoseconds (ns) RMS delay) across the surface of the array. Without being bound by theory, it is believed that can be due to a viscous silver epoxy that can be used for an electrode. Delay-and-sum focusing was degraded in CNR relative to DSIQ because a 4-cycle transmit pulse was used, versus a 2-cycle transmit pulse, verified by delay-and-sum simulation results with a 4-cycle transmit pulse.

Generally, without being bound by theory, it is believed that separable focusing decomposition can perform worst in conditions of low f-numbers, in the extreme near field (e.g., due to increased wavefront curvature), and at operating frequencies where grating lobes can be severe, such as indicated by the illustrative examples of FIGS. 8A through 8F. In such conditions, a separable delay-and-sum technique can still be only minimally degraded relative to non-separable delay-and-sum. When compared to delay-and-sum, separable DSIQ focusing, generally exhibits more significant degradation in the high-operating frequency, grating lobe condition, but generally performs acceptably in other configurations.

Separable focusing performance can be governed at least in part by a (separable) Fresnel approximation under imaging conditions. For example, a square root expansion of this form can converge more quickly when the term 'b' from EQN. (7) is relatively small. The variable 'b' can be related to the f-number used in the system, such as using EQN. (20), which for f/#=1.0 is approximately 0.354. For realistic apertures, such a series can converge rapidly, and the significance of later terms in the expansion can fall quickly.

$$b = \left(\sqrt{2}\frac{X^2}{Z_f^2}\right), f = \frac{Z_f}{2X} \therefore b = \sqrt{2}\frac{1}{4f^2} = \frac{1}{2\sqrt{2}f^2} \quad (20)$$

A non-separable part of the third term in the expansion, $2(\Delta X^2 \Delta Y^2/Z_f^2)$ can be significant compared to the separable part, $(\Delta X^2/Z_f^2+\Delta Y^2/Z_f^2)$, such as in the corners of the aperture. But, the corners of the aperture can have reduced effective sensitivity, such as because of apodization weighting or element directivity, so it is believed that such the approximation error can be mitigated.

Subaperture techniques can also be used, such as with plane wave-transmit, receive-only focusing. However, severe grating lobes can degrade imaging performance for such subaperture techniques.

Generally, decomposition of a 2D beamforming operation into two separable 1-D line array beamforming operations (e.g., a first set of sums, and a second sum using the first set of sums) can provide an order-of-magnitude performance increase for near-field wideband 3D ultrasound imaging. Such a 3D technique can include applying varying 'time delays' across the azimuthal dimension, such as followed by the application of further 'time delays' to the azimuthally delayed data, operating across the elevational dimension. For example, when the 'time delays' are phase rotations, as in a DSIQ focusing example, the two delays can be applied as successive complex multiplications.

However, when interpolation operations are used to sample time series at delays of up to tens of samples, a full, delayed time series history may generally be produced by the azimuthal focusing step before elevational focusing. Although the interpolations can be applied using short FIR filters at integer offsets for delay-and-sum focusing, the separable method applied to delay-and-sum generally includes a full time-series that can be produced by the first 1D focusing step. For volume focusing, this can represent oversampling in the axial dimension, detracting from the performance gains from separable decomposition, so that the separable method may be more desirably use with delay-and-sum for volume imaging modes, as compared to axial image sampling.

In contrast, separable DSIQ can focus volume data with specified axial plane spacing, such as to form single C-mode slices in isolation. For hand-held devices with limited power, DSIQ can be an effective way to use a 2D array for real-time imaging with multi-hour battery life (e.g., without requiring AC mains power). In addition to energy-efficient beamforming, front-end ASICs using the DSIQ sampling technique can consume very little power, such as using a low-duty-cycle operating mode.

In comparison to generally-available always-on ultrasound analog front-end integrated circuits, such as the Texas Instruments AFE 5807 (88 mW/channel at 40 MHz, 12-bit ADC) or the Analog Devices AD 9278 (also 88 mW/channel at 40 MHz, 12-bit ADC), a typical DSIQ front end can consume 13.8 µW per channel or less at about 30 frames/second, or about 1.6 mJ per frame to operate all 3600 channels for C-mode imaging. This can represent less than 1/6000 of the power of the always-on front-ends, and approximately 1/5 of the typical energy cost (7.5 mJ) of the separable DSIQ beamformer processing.

It is believed that separable 2D focusing can provide computational cost reduction of (M+N)/2 as compared to non-separable focusing, where M and N are the focusing aperture dimensions in elements. In an illustrative example of a 40×40 aperture, a significant speed-up of about 20 times is predicted. Experimentally-obtained speed increases ranged between 57%-87%, and 61%-89% of predicted values for delay-and-sum, and DSIQ focusing respectively, using SIMD optimization on compiled code for an OMAP processor circuit. In comparison, non-SIMD performance differs from predicted values by just 8% for delay- and sum, and 4% for DSIQ focusing. While not bound by theory, it is believed that this indicates that when SIMD instructions are used, giving a 2-3× speed increase, loop overhead becomes a performance bottleneck for smaller apertures.

In an illustrative example, an FFT-based 2D convolution on double precision data in MATLAB was 2.12 times slower compared to SDF for a 20×20 aperture and 1.64 times slower for a 40×40 aperture. For a short (32-64 element) 1D apertures, FFT-based 1D convolution can be comparable to non-FFT 1D convolution in computational cost. For 2D convolution, the FFT method computational cost generally can increase to $O(N^2 \log(N))$, while a separable 2D focusing cost generally can increase from $O(N^2)$ to $O((N+N)N^2)$ or $O(2N^3)$. Without being bound by theory, it is believed that zero-padding or significantly higher memory usage associated with FFT-based focusing (compared to SDF focusing) explains the performance advantage of the separable method for specified data sizes. It is believed that such a speed advantage for separable techniques can be become even more pronounced in processors with smaller L1 cache memories, such as those likely to be used in hand-held, battery-operated devices. While FFT approaches can be enhanced, such as using FPGAs, specialized DSPs or ASICs, performance increases suggested by FFT-based 2D convolution are not necessarily achievable on low-power processors suitable for hand-held devices.

Separable 2D beamforming can have minimal effect on imaging quality, such as indicated by simulated and experimentally-obtained cyst CNR values. A high quality interpolator can be used in DAS beamforming, to prevent cumulative interpolation errors from degrading imaging performance. DSIQ-based sampling techniques can be capable of achieving contrast levels approaching those of DAS, such as when two complex sample planes are captured and weighted appropriately. Although mainlobe width and sidelobe levels with DSIQ are generally worse than DAS, separable DSIQ can be used to form C-mode images or volume images with arbitrary axial sampling. In contrast, separable delay-and-sum can achieve large performance improvements when forming volume images, with additional axial sampling constraints due to the two-step focusing process.

Various Notes & Examples

Example 1 can include or use subject matter (such as an apparatus, a method, a means for performing acts, or a device readable medium including instructions that, when performed by the device, can cause the device to perform acts), such as can include or use an ultrasonic imaging system for use with an ultrasonic transducer array, the ultrasonic transducer array including transducer elements arranged in a two-dimensional array defining a transducer plane and configured to insonify a tissue region with ultrasonic energy, the system comprising a processor circuit configured to obtain, from the ultrasonic transducer array, information indicative of the reflected ultrasonic energy, including obtaining at least approximated complex samples of the reflected ultrasonic energy, and construct a representation of an imaging plane, within the tissue region, including using the obtained information indicative of the reflected ultrasonic energy including separately determining, for respective focusing locations in an imaging plane including a specified focusing location, respective first sums of at least approximated complex samples of reflected ultrasonic energy obtained via respective first lines of transducers in the ultrasonic transducer array, the at least approximated complex samples obtained via respective first lines of transducers corresponding to respective orthogonal projections of the respective focusing locations in the imaging plane onto the respective first lines in the transducer plane and separately determining, for the specified focusing location in the imaging plane, a second sum of at least some the respective first sums of at least approximated complex samples of reflected ultrasonic energy, the second sum corresponding to a second line of transducers in the ultrasonic transducer array, the second line of transducers aligned along an axis different from an axis of the respective first lines in the transducer plane and corresponding to the orthogonal projection of the specified focusing location in the imaging plane onto the transducer plane, the separately determining the first or second sums of at least approximated complex samples including phase-rotating at least some of the at least approximated complex samples.

Example 2 can include, or can optionally be combined with the subject matter of Example 1, to optionally include a processor circuit is configured to obtain at least approximated complex samples of the reflected ultrasonic energy using Direct-Sampled In-phase and Quadrature (DSIQ) sampling.

Example 3 can include, or can optionally be combined with the subject matter of one or any combination of Examples 1 or 2 to optionally include an ultrasonic transducer array, a display configured to display an image of the representation of the plane within the tissue region constructed by the processor circuit, the ultrasonic transducer array, processor, and processor comprise a hand-held assembly configured to operate without requiring power obtained contemporaneously from an Alternating Current (AC) mains supply.

Example 4 can include, or can optionally be combined with the subject matter of one or any combination of Examples 1 through 3 to optionally include phase-rotating at least some of the samples including determining a respective phase-rotation factors using a truncated Taylor series expansion corresponding to an approximation of a geometric acoustic propagation time delay from respective focusing locations to respective transducer locations, the truncated Taylor series expansion separated into a first set of respective phase rotations corresponding to respective at least approximated complex samples obtained via respective transducers comprising the respective first lines including an orthogonal projection of the respective focusing locations, and a second set of respective phase rotations corresponding to respective at least approximated complex samples obtained via respective transducer comprising the second line corresponding to an orthogonal projection of the specified focusing location onto the transducer array.

Example 5 can include, or can optionally be combined with the subject matter of one or any combination of Examples 1 through 4 to optionally include a processor circuit configured to construct a C-mode representation by, for each focusing location in a C-mode imaging plane separately determining respective first sums of at least approximated complex samples of reflected ultrasonic energy obtained via respective first lines of transducers, and separately determining respective second sums of the at least some of the respective first sums corresponding to respective second lines of transducers in the ultrasonic array corresponding to the orthogonal projection of a respective focusing location in the C-mode imaging plane onto the transducer array.

Example 6 can include, or can optionally be combined with the subject matter of one or any combination of Examples 1 through 5 to optionally include separately determining the respective first sums including using respective first apodization weighting factors specified corresponding to the respective first lines, and separately determining the second sum including using respective second apodization weighting factors specified corresponding to the second line.

Example 7 can include, or can optionally be combined with the subject matter of one or any combination of Examples 1 through 6 to optionally include a processor circuit configured to construct at least a portion of a first C-mode representation of at least a portion of a first plane at a first specified depth within the tissue region, and configured to construct at least a portion of a second C-mode representation of at least a portion of a second plane at a second specified depth within the tissue region.

Example 8 can include, or can optionally be combined with the subject matter of Example 7, to optionally include constructing a representation of a specified plane other than a C-mode imaging plane within the tissue using information from the first and second C-mode representations.

Example 9 can include, or can optionally be combined with the subject matter of one or any combination of Examples 1 through 8 to optionally include a processor circuit is configured to obtain information from the ultrasonic transducer array indicative of the reflected ultrasonic energy including obtaining a real time-series of samples of the reflected ultrasonic energy, the processor circuit configured to construct the representation of the imaging plane including determining a third sum of at least some of the real time-series of samples, the determining the third sum including applying a specified time delay to at least sonic of the real time-series of samples.

Example 10 can include, or can optionally be combined with the subject matter of one or any combination of Examples 1 through 9 to optionally include first lines orthogonal to the second line in the plane defined by the transducer array.

Example 11 can include, or can optionally be combined with the subject matter of one or any combination of Examples 1 through 10 to include, subject matter (such as an apparatus, a method, a means for performing acts, or a machine readable medium including instructions that, when performed by the machine, that can cause the machine to perform acts), such as can include ultrasonic imaging using an ultrasonic transducer array comprising transducer elements arranged in a two-dimensional array defining a transducer plane, the ultrasonic transducer array configured to insonify a tissue region with ultrasonic energy, comprising obtaining, from the ultrasonic transducer array, information indicative of the reflected ultrasonic energy, including obtaining at least approximated complex samples of the reflected ultrasonic energy, constructing a representation of an imaging plane, within the tissue region, including using the obtained information indicative of the reflected ultrasonic energy including separately determining, for respective focusing locations in an imaging plane including a specified focusing location, respective first sums of at least approximated complex samples of reflected ultrasonic energy obtained via respective first lines of transducers in the ultrasonic transducer array, the at least approximated complex samples obtained via respective first lines of transducers corresponding to respective orthogonal projections of the respective focusing locations in the imaging plane onto the respective first lines in the transducer plane, and separately determining, for the specified focusing location in the imaging plane, a second sum of at least some the respective first sums of at least approximated complex samples of reflected ultrasonic energy, the second sum corresponding to a second line of transducers in the ultrasonic transducer array, the second line of transducers aligned along an axis different from an axis of the respective first lines in the transducer plane and corresponding to the orthogonal projection of the specified focusing location in the imaging plane onto the transducer plane, the separately determining the first or second sums of at least approximated complex samples includes phase-rotating at least some of the at least approximated complex samples.

Example 12 can include, or can optionally be combined with the subject matter of Example 11 to optionally include obtaining at least approximated complex samples of the reflected ultrasonic energy using Direct-Sampled In-phase and Quadrature (DSIQ) sampling.

Example 13 can include, or can optionally be combined with the subject matter of one or any combination of Examples 11 or 12 to optionally include constructing the image plane representation using a hand-held assembly comprising a processor circuit and the transducer array, and displaying an image of the representation using the hand-held assembly, the hand-held assembly configured to operate without requiring power obtained contemporaneously from an Alternating Current (AC) mains supply.

Example 14 can include, or can optionally be combined with the subject matter of one or any combination of Examples 11 through 13 to optionally include phase-rotating at least some of the samples including determining a respective phase-rotation factors using a truncated Taylor series expansion corresponding to an approximation of a geometric acoustic propagation time delay from respective focusing locations to respective transducer locations, the truncated Taylor series expansion separated into a first set of respective phase rotations corresponding to respective at least approximated complex samples obtained via respective transducers comprising the respective first lines including an orthogonal projection of the respective focusing locations, and a second set of respective phase rotations corresponding to respective at least approximated complex samples obtained via respective transducer comprising the second line corresponding to an orthogonal projection of the specified focusing location onto the transducer array.

Example 15 can include, or can optionally be combined with the subject matter of one or any combination of Examples 11 through 14 to optionally include constructing a C-mode representation by, for each focusing location in a C-mode imaging plane, including separately determining respective first sums of at least approximated complex samples of reflected ultrasonic energy obtained via respective first lines of transducers, and separately determining respective second sums of the at least sonic of the respective first sums corresponding to respective second lines of transducers in the ultrasonic array corresponding to the orthogonal projection of a respective focusing location in the C-mode imaging plane onto the transducer array.

Example 16 can include, or can optionally be combined with the subject matter of one or any combination of Examples 11 through 15 to optionally include separately determining the respective first sums including using respective first apodization weighting factors specified corresponding to the respective first lines, and the separately determining the second sum including using respective second apodization weighting factors specified corresponding to the second line.

Example 17 can include, or can optionally be combined with the subject matter of one or any combination of Examples 11 through 16 to optionally include constructing at least a portion of a first C-mode representation of at least a portion of a first plane at a first specified depth within the tissue region, and configured to construct at least a portion of a second C-mode representation of at least a portion of a second plane at a second specified depth within the tissue region.

Example 18 can include, or can optionally be combined with the subject matter of Example 17, to optionally include constructing a representation of a specified plane other than a C-mode imaging plane within the tissue using information from the first and second C-mode representations.

Example 19 can include, or can optionally be combined with the subject matter of one or any combination of Examples 11 through 18 to optionally include obtaining information from the ultrasonic transducer array indicative of the reflected ultrasonic energy including obtaining a real time-series of samples of the reflected ultrasonic energy, and constructing the representation of the imaging plane including determining a third sum of at least some of the real time-series of samples, the determining the third sum including applying a specified time delay to at least some of the real time-series of samples.

Example 20 can include, or can optionally be combined with the subject matter of one or any combination of Examples 11 through 19 to optionally include first lines orthogonal to the second line in the plane defined by the transducer array.

Example 21 can include, or can optionally be combined with the subject matter of one or any combination of Examples 1 through 20 to include, subject matter (such as an apparatus, a method, a means for performing acts, or a machine readable medium including instructions that, when performed by the machine, that can cause the machine to perform acts), such as can include a processor-readable medium including instructions that, when performed by at least one processor included as a portion of a hand-held assembly, cause the hand-held assembly to control an ultrasonic transducer array included as a portion of the hand-held assembly to generate the ultrasonic energy or to receive reflected ultrasonic enemy, the ultrasonic transducer array comprising transducer elements arranged in a two-dimensional array comprising a transducer plane, the ultrasonic transducer array configured to insonify a tissue region with ultrasonic energy, obtain, from the ultrasonic transducer array, information indicative of the reflected ultrasonic energy, including obtaining at least approximated complex samples of the reflected ultrasonic energy using Direct-Sampled In-phase and Quadrature (DSIQ) sampling, and construct a representation of an imaging plane, within the tissue region, including using the obtained information indicative of the reflected ultrasonic energy including separately determining, for respective focusing locations in an imaging plane including a specified focusing location, respective first sums of at least approximated complex samples of reflected ultrasonic energy obtained via respective first lines of transducers in the ultrasonic transducer array, the at least approximated complex samples obtained via respective first lines of transducers corresponding to respective orthogonal projections of the respective focusing locations in the imaging plane onto the respective first lines in the transducer plane, and separately determining, for the specified focusing location in the imaging plane, a second sum of at least some the respective first sums of at least approximated complex samples of reflected ultrasonic energy, the second sum corresponding to a second line of transducers in the ultrasonic transducer array, the second line of transducers aligned along an axis different from an axis of the respective first lines in the transducer plane and corresponding to the orthogonal projection of the specified focusing location in the imaging plane onto the transducer plane, the separately determining the first or second sums of at least approximated complex samples including phase-rotating at least some of the at least approximated complex samples.

Example 22 can include, or can optionally be combined with the subject matter of Example 21, to optionally include instructions include instructions that cause the hand-held assembly to obtain information from the ultrasonic transducer array indicative of the reflected ultrasonic energy including obtaining a real time-series of samples of the reflected ultrasonic energy, and construct the representation of the imaging plane including determining a third sum of at least some of the real time-series of samples, the determining the third sum including applying a specified time delay to at least some of the real time-series of samples.

Example 23 can include, or can optionally be combined with the subject matter of one or any combination of Examples 21 or 22 to optionally include first lines orthogonal to the second line in the plane defined by the transducer array.

Example 24 can include, or can optionally be combined with any portion or combination of any portions of any one or more of Examples 1 through 23 to include, subject mater that can include means for performing any one or more of the functions of Examples 1 through 23, or a machine-readable medium including instructions that, when performed by a machine, cause the machine to perform any one or more of the functions of Examples 1 through 23. Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R., § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An ultrasonic imaging system for use with an ultrasonic transducer array, the ultrasonic transducer array including transducer elements arranged in a two-dimensional array defining a transducer plane and configured to insonify a tissue region with ultrasonic energy, the system comprising a processor circuit coupled to a memory circuit, the memory circuit comprising instructions that, when performed by the processor circuit, cause the processor circuit to:
   obtain, from the ultrasonic transducer array, information indicative of the reflected ultrasonic energy; and
   construct a representation of an imaging plane, within the tissue region, including using the obtained information indicative of the reflected ultrasonic energy including:
      separately determining, for respective focusing locations in an imaging plane including a specified focusing location, respective first sums of samples of reflected ultrasonic energy obtained via respective first lines of transducers in the ultrasonic transducer array, the samples obtained via respective first lines of transducers corresponding to respective orthogonal projections of the respective focusing locations in the imaging plane onto the respective first lines in the transducer plane; and
      separately determining, for the specified focusing location in the imaging plane, a second sum of at least some of the respective first sums of samples of reflected ultrasonic energy, the second sum corresponding to a second line of transducers in the ultrasonic transducer array, the second line of transducers aligned along an axis different from an axis of the respective first lines in the transducer plane and corresponding to the orthogonal projection of the specified focusing location in the imaging plane onto the transducer plane.

2. The ultrasound imaging system of claim 1, wherein the instructions comprise instructions to apply a phase rotation or a time delay to at least some of the samples including determining a phase rotation or a time delay determined from an approximation of a geometric acoustic propagation time delay from respective focusing locations to respective transducer locations.

3. The ultrasound imaging system of claim 1, wherein the instructions comprise instructions to construct a C-mode representation by, for each focusing location in a C-mode imaging plane:
   separately determining respective first sums of samples of reflected ultrasonic energy obtained via respective first lines of transducers; and
   separately determining respective second sums of the at least some of the respective first sums corresponding to respective second lines of transducers in the ultrasonic array corresponding to the orthogonal projection of a respective focusing location in the C-mode imaging plane onto the transducer array.

4. The ultrasound imaging system of claim 1, wherein the separately determining the respective first sums includes using respective first apodization weighting factors specified corresponding to the respective first lines; and
   wherein the separately determining the second sum includes using respective second apodization weighting factors specified corresponding to the second line.

5. The ultrasound imaging system of claim 1, wherein the instructions comprise instructions to:
   obtain information from the ultrasonic transducer array indicative of the reflected ultrasonic energy including obtaining a real-valued time-series of samples of the reflected ultrasonic energy; and construct the representation of the imaging plane including determining a third sum of at least some of the real-valued time-series of samples;
wherein the determining the third sum includes applying a specified time delay to at least some of the real-valued time-series of samples.

6. The ultrasound imaging system of claim 1, wherein the first lines are orthogonal to the second line in the plane defined by the transducer array.

7. The ultrasound imaging system of claim 1, comprising:
the ultrasonic transducer array; and
a display configured to display an image of the representation of the plane within the tissue region constructed by the processor circuit.

8. The ultrasound imaging system of claim 1, wherein the ultrasonic transducer array, processor circuit, and display comprise a hand-held assembly configured to operate without requiring power obtained contemporaneously from an Alternating Current (AC) mains supply.

9. The ultrasound imaging system of claim 1, wherein the samples include complex-valued samples having one or more of a real-valued part or an imaginary-valued part.

10. A method for ultrasonic imaging using an ultrasonic transducer array comprising transducer elements arranged in a two-dimensional array defining a transducer plane, the ultrasonic transducer array configured to insonify a tissue region with ultrasonic energy, the method comprising:
obtaining, from the ultrasonic transducer array, information indicative of the reflected ultrasonic energy; and
constructing a representation of an imaging plane, within the tissue region, including using the obtained information indicative of the reflected ultrasonic energy including:
separately determining, for respective focusing locations in an imaging plane including a specified focusing location, respective first sums of samples of reflected ultrasonic energy obtained via respective first lines of transducers in the ultrasonic transducer array, the samples obtained via respective first lines of transducers corresponding to respective orthogonal projections of the respective focusing locations in the imaging plane onto the respective first lines in the transducer plane; and
separately determining, for the specified focusing location in the imaging plane, a second sum of at least some of the respective first sums of samples of reflected ultrasonic energy, the second sum corresponding to a second line of transducers in the ultrasonic transducer array, the second line of transducers aligned along an axis different from an axis of the respective first lines in the transducer plane and corresponding to the orthogonal projection of the specified focusing location in the imaging plane onto the transducer plane.

11. The method of claim 10, comprising applying a phase rotation or a time delay to at least some of the samples including determining a phase rotation or a time delay determined from an approximation of a geometric acoustic propagation time delay from respective focusing locations to respective transducer locations.

12. The method of claim 10, wherein separately determining the respective first sums includes using respective first apodization weighting factors specified corresponding to the respective first lines; and
wherein the separately determining the second sum includes using respective second apodization weighting factors specified corresponding to the second line.

13. The method of claim 10, comprising:
obtaining information from the ultrasonic transducer array indicative of the reflected ultrasonic energy including obtaining a real-valued time-series of samples of the reflected ultrasonic energy; and
constructing the representation of the imaging plane including determining a third sum of at least some of the real-valued time-series of samples;
wherein the determining the third sum includes applying a specified time delay to at least some of the real-valued time-series of samples.

14. The method of claim 10, comprising:
constructing a C-mode representation by, for each focusing location in a C-mode imaging plane:
separately determining respective first sums of samples of reflected ultrasonic energy obtained via respective first lines of transducers; and
separately determining respective second sums of the at least some of the respective first sums corresponding to respective second lines of transducers in the ultrasonic array corresponding to the orthogonal projection of a respective focusing location in the C-mode imaging plane onto the transducer array.

15. The method of claim 10, comprising constructing at least a portion of a first C-mode representation of at least a portion of a first plane at a first specified depth within the tissue region, and configured to construct at least a portion of a second C-mode representation of at least a portion of a second plane at a second specified depth within the tissue region.

16. The method of claim 10, comprising constructing a representation of a specified plane other than a C-mode imaging plane within the tissue using information from the first and second C-mode representations.

17. The method of claim 10, wherein the first lines are orthogonal to the second line in the plane defined by the transducer array.

18. The method of claim 10, wherein the samples include complex-valued samples having one or more of a real-valued part or an imaginary-valued part.

* * * * *